United States Patent
Bardy et al.

(10) Patent No.: US 9,545,228 B2
(45) Date of Patent: *Jan. 17, 2017

(54) EXTENDED WEAR ELECTROCARDIOGRAPHY AND RESPIRATION-MONITORING PATCH

(71) Applicant: Bardy Diagnostics, Inc., Vashon, WA (US)

(72) Inventors: Gust H. Bardy, Carnation, WA (US); Jon Mikalson Bishay, Seattle, WA (US); Jason Felix, Vashon, WA (US)

(73) Assignee: BARDY DIAGNOSTICS, INC., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/181,082

(22) Filed: Jun. 13, 2016

(65) Prior Publication Data

US 2016/0296166 A1     Oct. 13, 2016

Related U.S. Application Data

(63) Continuation of application No. 14/082,102, filed on Nov. 15, 2013, now Pat. No. 9,364,155, which is a
(Continued)

(51) Int. Cl.
*A61B 5/00* (2006.01)
*A61B 5/0205* (2006.01)
(Continued)

(52) U.S. Cl.
CPC ........... *A61B 5/4818* (2013.01); *A61B 5/0022* (2013.01); *A61B 5/02055* (2013.01);
(Continued)

(58) Field of Classification Search
CPC . A61B 5/0006; A61B 5/0022; A61B 5/02055; A61B 5/03; A61B 5/04085; A61B 5/04087; A61B 5/04325; A61B 5/087; A61B 5/1118; A61B 5/14532; A61B 5/14551; A61B 5/4818; A61B 5/7282; A61B 5/6832; A61B 5/14552

See application file for complete search history.

(56) References Cited

U.S. PATENT DOCUMENTS

| 3,215,136 A | 11/1965 | Holter et al. |
| 3,699,948 A | 10/1972 | Ota et al. |

(Continued)

FOREIGN PATENT DOCUMENTS

| DE | 19955211 | 5/2001 |
| EP | 1859833 | 11/2007 |

(Continued)

OTHER PUBLICATIONS

US 6,527,714, 03/2003, Bardy (withdrawn)
(Continued)

*Primary Examiner* — George Manuel
(74) *Attorney, Agent, or Firm* — Patrick J. S. Inouye; Leonid Kisselev

(57) ABSTRACT

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum) benefits extended wear by removing the requirement that ECG electrodes be continually placed in the same spots on the skin throughout the monitoring period. Instead, the patient can place an electrode patch anywhere within the general region of the sternum. Power is provided through a battery provided on the electrode patch, which (Continued)

avoids having to open the monitor recorder's housing for battery replacement. The patch further includes sensors for monitoring patient's air flow and respiratory measures contemporaneously with the ECG monitoring.

20 Claims, 13 Drawing Sheets

Related U.S. Application Data continuation-in-part of application No. 14/080,717, filed on Nov. 14, 2013, which is a continuation-in-part of application No. 14/080,725, filed on Nov. 14, 2013.

(60) Provisional application No. 61/882,403, filed on Sep. 25, 2013.

(51) Int. Cl.
  *A61B 5/0408*  (2006.01)
  *A61B 5/087*  (2006.01)
  *A61B 5/145*  (2006.01)
  *A61B 5/1455*  (2006.01)

(52) U.S. Cl.
  CPC .......... *A61B 5/04085* (2013.01); *A61B 5/087* (2013.01); *A61B 5/14532* (2013.01); *A61B 5/14552* (2013.01); *A61B 5/6832* (2013.01)

(56) References Cited

U.S. PATENT DOCUMENTS

| | | | |
|---|---|---|---|
| 3,893,453 | A | 7/1975 | Goldberg |
| 4,123,785 | A | 10/1978 | Cherry et al. |
| 4,328,814 | A | 5/1982 | Arkans |
| 4,532,934 | A | 8/1985 | Kelen |
| 4,550,502 | A | 11/1985 | Grayzel |
| 4,716,903 | A | 1/1988 | Hansen |
| 4,809,705 | A | 3/1989 | Ascher |
| 4,915,656 | A | 4/1990 | Alferness |
| 5,025,794 | A | 6/1991 | Albert et al. |
| 5,168,876 | A | 12/1992 | Quedens et al. |
| 5,215,098 | A | 6/1993 | Steinhaus |
| D341,423 | S | 11/1993 | Bible |
| 5,341,806 | A | 8/1994 | Gadsby et al. |
| 5,355,891 | A | 10/1994 | Wateridge et al. |
| 5,365,934 | A | 11/1994 | Leon et al. |
| 5,392,784 | A | 2/1995 | Gudaitis |
| D357,069 | S | 4/1995 | Plahn et al. |
| 5,402,780 | A | 4/1995 | Faasse, Jr. |
| 5,402,884 | A | 4/1995 | Gilman et al. |
| 5,450,845 | A | 9/1995 | Axelgaard |
| 5,458,141 | A | 10/1995 | Neil |
| 5,473,537 | A | 12/1995 | Glazer et al. |
| 5,483,969 | A | 1/1996 | Testerman et al. |
| 5,511,553 | A | 4/1996 | Segalowitz |
| 5,540,733 | A | 7/1996 | Testerman et al. |
| 5,546,952 | A | 8/1996 | Erickson |
| 5,549,655 | A | 8/1996 | Erickson |
| 5,579,919 | A | 12/1996 | Gilman et al. |
| 5,582,181 | A | 12/1996 | Ruess |
| D377,983 | S | 2/1997 | Sabri et al. |
| 5,601,089 | A | 2/1997 | Bledsoe et al. |
| 5,623,935 | A | 4/1997 | Faisandier |
| 5,682,901 | A | 11/1997 | Kamen |
| 5,697,955 | A | 12/1997 | Stolte |
| 5,749,902 | A | 5/1998 | Olsen et al. |
| 5,817,151 | A | 10/1998 | Olsen et al. |
| 5,819,741 | A | 10/1998 | Karlsson et al. |
| 5,850,920 | A | 12/1998 | Gilman et al. |
| D407,159 | S | 3/1999 | Roberg |
| 5,906,583 | A | 5/1999 | Rogel |
| 5,951,598 | A | 9/1999 | Bishay et al. |
| 5,957,857 | A | 9/1999 | Hartley |
| 5,984,102 | A | 11/1999 | Tay |
| 6,032,064 | A | 2/2000 | Devlin et al. |
| 6,038,469 | A | 3/2000 | Karlsson et al. |
| 6,101,413 | A | 8/2000 | Olsen et al. |
| 6,115,638 | A | 9/2000 | Groenke |
| 6,117,077 | A | 9/2000 | Del Mar et al. |
| 6,134,479 | A | 10/2000 | Brewer et al. |
| 6,148,233 | A | 11/2000 | Owen et al. |
| 6,149,602 | A | 11/2000 | Arcelus |
| 6,149,781 | A | 11/2000 | Forand |
| 6,188,407 | B1 | 2/2001 | Smith et al. |
| D443,063 | S | 5/2001 | Pisani et al. |
| 6,245,025 | B1 | 6/2001 | Torok et al. |
| 6,246,330 | B1 | 6/2001 | Nielsen |
| D445,507 | S | 7/2001 | Pisani et al. |
| 6,269,267 | B1 | 7/2001 | Bardy et al. |
| 6,272,385 | B1 | 8/2001 | Bishay et al. |
| 6,298,255 | B1 | 10/2001 | Cordero et al. |
| 6,301,502 | B1 | 10/2001 | Owen et al. |
| 6,304,773 | B1 | 10/2001 | Taylor et al. |
| 6,304,780 | B1 | 10/2001 | Owen et al. |
| 6,304,783 | B1 | 10/2001 | Lyster et al. |
| 6,374,138 | B1 | 4/2002 | Owen et al. |
| 6,416,471 | B1 | 7/2002 | Kumar et al. |
| 6,418,342 | B1 | 7/2002 | Owen et al. |
| 6,424,860 | B1 | 7/2002 | Karlsson et al. |
| 6,427,083 | B1 | 7/2002 | Owen et al. |
| 6,456,872 | B1 | 9/2002 | Faisandier |
| 6,546,285 | B1 | 4/2003 | Owen et al. |
| 6,605,046 | B1 | 8/2003 | Del Mar |
| 6,607,485 | B2 | 8/2003 | Bardy |
| 6,611,705 | B2 | 8/2003 | Hopman et al. |
| 6,671,545 | B2 | 12/2003 | Fincke |
| 6,671,547 | B2 | 12/2003 | Lyster et al. |
| 6,694,186 | B2 | 2/2004 | Bardy |
| 6,704,595 | B2 | 3/2004 | Bardy |
| 6,705,991 | B2 | 3/2004 | Bardy |
| 6,719,701 | B2 | 4/2004 | Lade |
| 6,754,523 | B2 | 6/2004 | Toole |
| 6,782,293 | B2 | 8/2004 | Dupelle et al. |
| 6,856,832 | B1 | 2/2005 | Matsumura et al. |
| 6,860,897 | B2 | 3/2005 | Bardy |
| 6,866,629 | B2 | 3/2005 | Bardy |
| 6,887,201 | B2 | 5/2005 | Bardy |
| 6,893,397 | B2 | 5/2005 | Bardy |
| 6,904,312 | B2 | 6/2005 | Bardy |
| 6,908,431 | B2 | 6/2005 | Bardy |
| 6,913,577 | B2 | 7/2005 | Bardy |
| 6,944,498 | B2 | 9/2005 | Owen et al. |
| 6,960,167 | B2 | 11/2005 | Bardy |
| 6,970,731 | B1 | 11/2005 | Jayaraman et al. |
| 6,978,169 | B1 | 12/2005 | Guerra |
| 6,993,377 | B2 | 1/2006 | Flick et al. |
| 7,020,508 | B2 | 3/2006 | Stivoric et al. |
| 7,027,864 | B2 | 4/2006 | Snyder et al. |
| 7,065,401 | B2 | 6/2006 | Worden |
| 7,085,601 | B1 | 8/2006 | Bardy et al. |
| 7,104,955 | B2 | 9/2006 | Bardy |
| 7,134,996 | B2 | 11/2006 | Bardy |
| 7,137,389 | B2 | 11/2006 | Berthon-Jones |
| 7,147,600 | B2 | 12/2006 | Bardy |
| 7,215,991 | B2 | 5/2007 | Besson et al. |
| 7,248,916 | B2 | 7/2007 | Bardy |
| 7,257,438 | B2 | 8/2007 | Kinast |
| 7,277,752 | B2 | 10/2007 | Matos |
| D558,882 | S | 1/2008 | Brady |
| 7,328,061 | B2 | 2/2008 | Rowlandson et al. |
| 7,412,395 | B2 | 8/2008 | Rowlandson et al. |
| 7,429,938 | B1 | 9/2008 | Corndorf |
| 7,552,031 | B2 | 6/2009 | Vock et al. |
| D606,656 | S | 12/2009 | Kobayashi et al. |
| 7,706,870 | B2 | 4/2010 | Shieh et al. |
| 7,756,721 | B1 | 7/2010 | Falchuk et al. |
| 7,787,943 | B2 | 8/2010 | McDonough |
| 7,874,993 | B2 | 1/2011 | Bardy |
| 7,881,785 | B2 | 2/2011 | Nassif et al. |
| D639,437 | S | 6/2011 | Bishay et al. |
| 7,959,574 | B2 | 6/2011 | Bardy |
| 8,116,841 | B2 | 2/2012 | Bly et al. |

(56) References Cited

U.S. PATENT DOCUMENTS

| | | |
|---|---|---|
| 8,150,502 B2 | 4/2012 | Kumar et al. |
| 8,160,682 B2 | 4/2012 | Kumar et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegel et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,554,311 B2 | 10/2013 | Warner et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,668,653 B2 | 3/2014 | Nagata et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,277,864 B2 | 3/2016 | Yang et al. |
| 9,339,202 B2 | 5/2016 | Brockway et al. |
| 2002/0013538 A1 | 1/2002 | Teller |
| 2002/0013717 A1 | 1/2002 | Ando et al. |
| 2002/0103422 A1 | 8/2002 | Harder et al. |
| 2002/0120310 A1 | 8/2002 | Linden et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0073916 A1 | 4/2003 | Yonce |
| 2003/0083559 A1 | 5/2003 | Thompson |
| 2003/0097078 A1 | 5/2003 | Maeda et al. |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0093192 A1 | 5/2004 | Hasson et al. |
| 2004/0148194 A1 | 7/2004 | Wellons et al. |
| 2004/0207530 A1 | 10/2004 | Nielsen |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0096717 A1 | 5/2005 | Bishay et al. |
| 2005/0108055 A1 | 5/2005 | Ott et al. |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0228243 A1 | 10/2005 | Bardy |
| 2005/0245839 A1 | 11/2005 | Stivoric et al. |
| 2006/0025696 A1 | 2/2006 | Kurzweil et al. |
| 2006/0025824 A1 | 2/2006 | Freeman et al. |
| 2006/0041201 A1 | 2/2006 | Behbehani et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0235320 A1 | 10/2006 | Tan et al. |
| 2006/0253006 A1 | 11/2006 | Bardy |
| 2006/0264730 A1 | 11/2006 | Stivoric et al. |
| 2007/0003115 A1 | 1/2007 | Patton et al. |
| 2007/0050209 A1 | 3/2007 | Yered |
| 2007/0078324 A1 | 4/2007 | Wijisiriwardana |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1 | 9/2007 | Kumar et al. |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0051668 A1 | 2/2008 | Bardy |
| 2008/0058661 A1 | 3/2008 | Bardy |
| 2008/0091097 A1 | 4/2008 | Linti et al. |
| 2008/0139953 A1 | 6/2008 | Baker et al. |
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0306359 A1 | 12/2008 | Zdeblick et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1 | 5/2009 | Sims et al. |
| 2009/0216132 A1 | 8/2009 | Orbach |
| 2009/0270708 A1 | 10/2009 | Shen et al. |
| 2009/0270747 A1 | 10/2009 | Van Dam et al. |
| 2009/0292194 A1 | 11/2009 | Libbus et al. |

(56) References Cited

U.S. PATENT DOCUMENTS

| | | | |
|---|---|---|---|
| 2010/0007413 A1 | 1/2010 | Herleikson et al. |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0234715 A1 | 9/2010 | Shin et al. |
| 2010/0234716 A1 | 9/2010 | Engel |
| 2010/0280366 A1 | 11/2010 | Arne et al. |
| 2010/0324384 A1 | 12/2010 | Moon et al. |
| 2011/0054286 A1 | 3/2011 | Crosby et al. |
| 2011/0066041 A1 | 3/2011 | Pandia et al. |
| 2011/0077497 A1 | 3/2011 | Oster et al. |
| 2011/0144470 A1 | 6/2011 | Mazar et al. |
| 2011/0160548 A1 | 6/2011 | Forster et al. |
| 2011/0224564 A1 | 9/2011 | Moon et al. |
| 2011/0237924 A1 | 9/2011 | McGusty et al. |
| 2011/0245699 A1 | 10/2011 | Snell et al. |
| 2011/0245711 A1 | 10/2011 | Katra et al. |
| 2012/0003933 A1 | 1/2012 | Baker et al. |
| 2012/0029306 A1 | 2/2012 | Paquet et al. |
| 2012/0029316 A1 | 2/2012 | Raptis et al. |
| 2012/0035432 A1 | 2/2012 | Katra et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1 | 4/2012 | Solosko et al. |
| 2012/0302906 A1 | 11/2012 | Felix et al. |
| 2012/0330126 A1* | 12/2012 | Hoppe ............... A61B 5/0002 600/391 |
| 2013/0079611 A1 | 3/2013 | Besko |
| 2013/0085403 A1 | 4/2013 | Gunderson et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0225963 A1 | 8/2013 | Kodandaramaiah et al. |
| 2013/0243105 A1 | 9/2013 | Lei et al. |
| 2013/0274584 A1 | 10/2013 | Finlay et al. |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2014/0012154 A1 | 1/2014 | Mazar et al. |
| 2014/0140359 A1 | 5/2014 | Kalevo et al. |
| 2014/0189928 A1 | 7/2014 | Oleson et al. |
| 2014/0206977 A1 | 7/2014 | Bahney et al. |
| 2014/0358193 A1 | 12/2014 | Lyons et al. |
| 2015/0048836 A1 | 2/2015 | Guthrie et al. |
| 2015/0165211 A1 | 6/2015 | Naqvi et al. |
| 2015/0257670 A1 | 9/2015 | Ortega et al. |
| 2015/0359489 A1 | 12/2015 | Baudenbacher et al. |

FOREIGN PATENT DOCUMENTS

| | | |
|---|---|---|
| EP | 2438851 | 4/2012 |
| EP | 2438852 | 4/2012 |
| EP | 2465415 | 6/2012 |
| EP | 2589333 | 5/2013 |
| JP | H06319711 | 11/1994 |
| JP | 2004129788 | 4/2004 |
| WO | 0078213 | 12/2000 |
| WO | 03032192 | 4/2003 |
| WO | 2006009767 | 1/2006 |
| WO | 2006014806 | 2/2006 |
| WO | 2007066270 | 6/2007 |
| WO | 2007092543 | 8/2007 |
| WO | 2008010216 | 1/2008 |
| WO | 2008057884 | 5/2008 |
| WO | 2009036306 | 3/2009 |
| WO | 2009036327 | 3/2009 |
| WO | 2009112976 | 9/2009 |
| WO | 2009112978 | 9/2009 |
| WO | 2009112979 | 9/2009 |
| WO | 2009142975 | 11/2009 |
| WO | 2010066507 | 6/2010 |
| WO | 2010105045 | 9/2010 |
| WO | 2011047207 | 4/2011 |
| WO | 2012140559 | 10/2012 |
| WO | 2012146957 | 11/2012 |

OTHER PUBLICATIONS

Duttweiler et al., "Probability Estimation in Arithmetic and Adaptive-Huffman Entropy Coders," IEEE Transactions on Image Processing. vol. 4, No. 3, Mar. 1, 1995, pp. 237-246.

Gupta et al., "An ECG Compression Technique for Telecardiology Application," India Conference (INDICON), 2011 Annual IEEE, Dec. 16, 2011, pp. 1-4.

Nave et al., "ECG Compression Using Long-Term Prediction," IEEE Transactions on Biomedical Engineering, IEEE Service Center, NY, USA, vol. 40, No. 9, Sep. 1, 1993, pp. 877-885.

Skretting et al., "Improved Huffman Coding Using Recursive Splitting," NORSIG, Jan. 1, 1999.

A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/i.1399-5618.2006.00364.x.

"Varicrad-Kardi Software User's Manual Rev. 1.1", Jul. 8, 2009 (Jul. 8, 2009), XP002757888, retrieved from the Internet: URL:http://www.ehrlich.tv/KARDiVAR-Software.pdf [retrieved on May 20, 2016].

15 of the Hottest Wearable Gadgets, URL <http://thehottestgadgets.com/2008/09/the-15-hottest-wearable-gadgets-001253> (Web page cached on Sep. 27, 2008).

Alivecor's Heart Monitor for iPhone Receives FDA Clearance, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).

Bharadwaj et al., Techniques for Accurate ECG signal processing, EE Times, URL <www.eetimes.com/document.asp?doc_id=1278571> (Feb. 14, 2011).

Chen et al., "Monitoring Body Temperature of Newborn Infants at Neonatal Intensive Care Units Using Wearable Sensors," BodyNets 2010, Corfu Island, Greece. (Sep. 10, 2010).

Epstein, Andrew E et al.; ACC/AHA/HRS 2008 Guidelines for Device-Based Therapy of Cardiac Rhythm Abnormalities. J. Am. Coll. Cardiol. 2008; 51; el-e62, 66 Pgs.

Fitbit automatically tracks your fitness and sleep, URL <http://www.fitbit.com/> (Web page cached on Sep. 10, 2008).

Smith, Kevin, "Jawbone Up vs. Fitbit Flex: Which is the Best Fitness Band?" URL <http://www.businessinsider.com/fitbit-flex-vs-jawbone-up-2013-5?op=1> (Jun. 1, 2013).

Kligfield, Paul et al., Recommendations for the Standardization and Interpretation of the Electrocardiogram: Part I. J.Am.Coll. Cardiol; 2007; 49; 1109-27, 75 Pgs.

Lauren Gravitz, "When Your Diet Needs a Band-Aid," Technology Review, MIT. (May 1, 2009).

Lieberman, Jonathan, "How Telemedicine is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.

McManus et al., "A Novel Application for the Detection of an Irregular Pulse using an iPhone 4S in Patients with Atrial Fibrillation," vol. 10(3), pp. 315-319 (Mar. 2013).

(56) References Cited

OTHER PUBLICATIONS

Nike+ Fuel Band, URL <http://www.nike.com/us/en_us/c/nikeplus-fuelband> (Web page cached on Jan. 11, 2013).

P. Libby et al.,"Braunwald's Heart Disease—A Textbook of Cardiovascular Medicine," Chs. 11, pp. 125-148 and 12, pp. 149-193 (8th ed. 2008), American Heart Association.

Initial hands-on with Polar Loop activity tracker, URL <http://www.dcrainmaker.com/2013/09/polar-loop-firstlook.html> (Sep. 17, 2013).

Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.

Sleepview, URL <http://www.clevemed.com/sleepview/overview.shtml> (Web pages cached on Feb. 23, 2010, Dec. 29, 2012 and Sep. 4, 2013).

Actigraphy/ Circadian Rhythm SOMNOwatch, URL <http://www.somnomedics.eu/news-events/publications/somnowatchtm.html> (Web page cached on Jan. 23, 2010).

Zio Event Card, URL <http://www.irhythmtech.com/zio-solution/zio-event/> (Web page cached on Mar. 11, 2013).

Zio Patch System, URL <http://www.irhythmtech.com/zio-solution/zio-system/index.html> (Web page cached on Sep. 8, 2013).

Seifert, Dan, "Samsung dives into fitness wearable with the Gear Fit/ The Verge," URL <http://www.theverge.com/2014/2/24/5440310/samsung-dives-into-fitness-wearables-with-the-gear-fit> (Feb. 24, 2014).

Soper, Taylor, "Samsung's new Galaxy S5 flagship phone has fingerprint reader, heart rate monitor," URL <http://www.geekwire.com/2014/samsung-galaxy-s5-fingerprint> (Feb. 24, 2014).

Dolcourt, Jessica, "See the Samsung Galaxy S5's Heart rate monitor in action," URL <http://www.cnet.com/news/see-the-samsung-galaxy-s5s-heart-rate-monitor-in-action> (Feb. 25, 2014).

Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.

Anonymous. Omegawave Launches Consumer App 2.0 in U.S. "Endurance Sportswire—Endurance Sportswire." Jul. 11, 2013. URL:http://endurancesportswire.com/omegawave-launches-consumer-app-2-0-in-u-s/.

Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.

Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.

Daoud et al. "Fall Detection Using Shimmer Technology and Multiresolution Analysis." Aug. 2, 2013. URL: https://decibel.ni.com/content/docs/DOC-26652.

Libbus. "Adherent Cardiac Monitor With Wireless Fall Detection for Patients With Unexplained Syncope." Abstracts of the First AMA-IEEE Medical Technology Conference on Individualized Healthcare. May 22, 2010.

Health Research—Hexoskin Biometric Shirt | Hexoskin URL:http://www.hexoskin.com/pages/health-research (Web page cached on Dec. 2, 2014).

Jacob Kastrenakes, "Apple Watch uses four sensors to detect your pulse," Sep. 9, 2014. URL: http://www.theverge.com/2014/9/9/6126991/apple-watch-four-back-sensors-detect-activity.

Nicole Lee, "Samsung gear S review: an ambitous and painfully flawed smartwatch," Dec. 1, 2014. URL: http://www.engadget.com/2014/12/01/samsung-gear-s-review/.

* cited by examiner

160

EXTENDED WEAR ELECTROCARDIOGRAPHY AND RESPIRATION-MONITORING PATCH

CROSS-REFERENCE TO RELATED APPLICATION

This non-provisional patent application is a continuation of U.S. patent No. 9,364,155, issued Jun. 14, 2016, which is a continuation-in-part of U.S. patent application Ser. No. 14/080,717, filed Nov. 14, 2013, pending, and which is also a continuation-in-part of U.S. patent application Ser. No. 14/080,725, filed Nov. 14, 2013, pending, and further claims priority under 35 U.S.C. §119(e) to U.S. Provisional Patent application, Ser. No. 61/882,403, filed Sep. 25, 2013, the disclosures of which are incorporated by reference.

FIELD

This application relates in general to electrocardiographic monitoring and, in particular, to an extended wear electrocardiography and respiration-monitoring patch.

BACKGROUND

The heart emits electrical signals as a by-product of the propagation of the action potentials that trigger depolarization of heart fibers. An electrocardiogram (ECG) measures and records such electrical potentials to visually depict the electrical activity of the heart over time. Conventionally, a standardized set format 12-lead configuration is used by an ECG machine to record cardiac electrical signals from well-established traditional chest locations. Electrodes at the end of each lead are placed on the skin over the anterior thoracic region of the patient's body to the lower right and to the lower left of the sternum, on the left anterior chest, and on the limbs. Sensed cardiac electrical activity is represented by PQRSTU waveforms that can be interpreted post-ECG recordation to derive heart rate and physiology. The P-wave represents atrial electrical activity. The QRSTU components represent ventricular electrical activity.

An ECG is a tool used by physicians to diagnose heart problems and other potential health concerns. An ECG is a snapshot of heart function, typically recorded over 12 seconds, that can help diagnose rate and regularity of heartbeats, effect of drugs or cardiac devices, including pacemakers and implantable cardioverter-defibrillators (ICDs), and whether a patient has heart disease. ECGs are used in-clinic during appointments, and, as a result, are limited to recording only those heart-related aspects present at the time of recording. Sporadic conditions that may not show up during a spot ECG recording require other means to diagnose them. These disorders include fainting or syncope; rhythm disorders, such as tachyarrhythmias and bradyarrhythmias; apneic episodes; and other cardiac and related disorders. Thus, an ECG only provides a partial picture and can be insufficient for complete patient diagnosis of many cardiac disorders.

The inadequacy of conventional, short-term, ECG recordings is particularly apparent in the case of sleep apnea, a type of sleep disorder that affects a patient's breathing during sleep and may also impact the patient's cardiac activity. ECG monitoring alone may not be useful in diagnosing the condition due to a natural heart rate reduction during sleep. As a patient enters non-rapid eye movement (NREM) sleep, the patient experiences physiological changes due to a withdrawal of activity of the patient's sympathetic nervous system. As a result, even healthy people may experience sinus bradyarrhythmia during sleep, and ECG monitoring alone may not always reveal whether the bradyarrhythmia is naturally-occurring or is caused by a pathological condition, such as an apneic episode. Furthermore, if the patient experiences other types of arrhythmias during sleep, without having a telemetry of the patient's air flow, the flow of air in and out of the patient's lungs during breathing, or another indicator of the patient's respiration, the physician may not be always able to determine if an arrhythmia is a result of a sleep apnea episode or of some other morbidity. However, considering that cardiac manifestations of sleep apnea are most apparent at night, a short-term ECG monitoring done in a clinic during business hours may not reveal even the presence of the cardiac arrhythmia.

Diagnostic efficacy can be improved, when appropriate, through the use of long-term extended ECG monitoring coupled to pulmonary measures. Recording sufficient ECG and related physiology over an extended period is challenging, and often essential to enabling a physician to identify events of potential concern. A 30-day observation period is considered the "gold standard" of ECG monitoring, yet achieving a 30-day observation day period has proven unworkable because such ECG monitoring systems are arduous to employ, cumbersome to the patient, and excessively costly. Ambulatory monitoring in-clinic is implausible and impracticable. Nevertheless, if a patient's ECG and pulmonary measures could be recorded in an ambulatory setting, thereby allowing the patient to engage in activities of daily living, the chances of acquiring meaningful information and capturing an abnormal event while the patient is engaged in normal activities becomes more likely to be achieved.

For instance, the long-term wear of ECG electrodes is complicated by skin irritation and the inability ECG electrodes to maintain continual skin contact after a day or two. Moreover, time, dirt, moisture, and other environmental contaminants, as well as perspiration, skin oil, and dead skin cells from the patient's body, can get between an ECG electrode, the non-conductive adhesive used to adhere the ECG electrode, and the skin's surface. All of these factors adversely affect electrode adhesion and the quality of cardiac signal recordings. Furthermore, the physical movements of the patient and their clothing impart various compressional, tensile, and torsional forces on the contact point of an ECG electrode, especially over long recording times, and an inflexibly fastened ECG electrode will be prone to becoming dislodged. Notwithstanding the cause of electrode dislodgment, depending upon the type of ECG monitor employed, precise re-placement of a dislodged ECG electrode maybe essential to ensuring signal capture at the same fidelity. Moreover, dislodgment may occur unbeknownst to the patient, making the ECG recordings worthless. Further, some patients may have skin that is susceptible to itching or irritation, and the wearing of ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleansing of the skin, allow for showering and exercise, or for other purpose. Such replacement or slight alteration in electrode location actually facilitates the goal of recording the ECG signal for long periods of time.

Conventionally, Holter monitors are widely used for long-term extended ECG monitoring. Typically, they are used for only 24-48 hours. A typical Holter monitor is a wearable and portable version of an ECG that include cables for each electrode placed on the skin and a separate battery-powered ECG recorder. The cable and electrode combination (or leads) are placed in the anterior thoracic region in a manner similar to what is done with an in-clinic standard ECG machine. The duration of a Holter monitoring recording depends on the sensing and storage capabilities of the monitor, as well as battery life. A "looping" Holter monitor (or event) can operate for a longer period of time by overwriting older ECG tracings, thence "recycling" storage in favor of extended operation, yet at the risk of losing event data. Although capable of extended ECG monitoring, Holter monitors are cumbersome, expensive and typically only available by medical prescription, which limits their usability. Further, the skill required to properly place the electrodes on the patient's chest hinders or precludes a patient from replacing or removing the precordial leads and usually involves moving the patient from the physician office to a specialized center within the hospital or clinic. Also, Holter monitors do not provide information about the patient's air flow, further limiting their usefulness in diagnosing the patient.

The ZIO XT Patch and ZIO Event Card devices, manufactured by iRhythm Tech., Inc., San Francisco, Calif., are wearable stick-on monitoring devices that are typically worn on the upper left pectoral region to respectively provide continuous and looping ECG recording. The location is used to simulate surgically implanted monitors. Both of these devices are prescription-only and for single patient use. The ZIO XT Patch device is limited to a 14-day monitoring period, while the electrodes only of the ZIO Event Card device can be worn for up to 30 days. The ZIO XT Patch device combines both electronic recordation components, including battery, and physical electrodes into a unitary assembly that adheres to the patient's skin. The ZIO XT Patch device uses adhesive sufficiently strong to support the weight of both the monitor and the electrodes over an extended period of time and to resist disadherance from the patient's body, albeit at the cost of disallowing removal or relocation during the monitoring period. Moreover, throughout monitoring, the battery is continually depleted and battery capacity can potentially limit overall monitoring duration. The ZIO Event Card device is a form of downsized Holter monitor with a recorder component that must be removed temporarily during baths or other activities that could damage the non-waterproof electronics. Both devices represent compromises between length of wear and quality of ECG monitoring, especially with respect to ease of long term use, female-friendly fit, and quality of atrial (P-wave) signals. Furthermore, both devices do not monitor the patient's air flow, further limiting their usefulness in diagnosing the patient.

While portable devices that combine respiratory and cardiac monitoring exist, these devices are also generally inadequate for long-term monitoring due to their inconvenience and restraint that they place on the patient's movements. For example, SleepView monitor devices, manufactured by Cleveland Medical Devices Inc. of Cleveland, Ohio, require a patient to wear multiple sensors on the patient's body, including a belt on the patient's chest, a nasal cannula, and an oximetry sensor on the patient's finger, with these sensors being connected by tubing and wires to a recording device worn on the belt. Having to wear these sensors throughout the patient's body limits the patient's mobility and may be embarrassing to the patient if worn in public, deterring the patient from undergoing such a monitoring for an extended period of time.

Therefore, a need remains for a self-contained personal air flow monitor capable of recording both air flow data, other respiratory data such as respiratory rate and effort, and ECG data, practicably capable of being worn for a long period of time in both men and women, and capable of recording atrial signals reliably.

A further need remains for a device capable of recording signals ideal for arrhythmia discrimination, especially a device designed for atrial activity recording, as the arrhythmias are coupled to the associated pulmonary problems common to sleep apnea and other respiratory disorders.

SUMMARY

Physiological monitoring can be provided through a wearable monitor that includes two components, a flexible extended wear electrode patch and a removable reusable monitor recorder. The wearable monitor sits centrally (in the midline) on the patient's chest along the sternum oriented top-to-bottom. The placement of the wearable monitor in a location at the sternal midline (or immediately to either side of the sternum), with its unique narrow "hourglass"-like shape, benefits long-term extended wear by removing the requirement that ECG electrodes be continually placed in the same spots on the skin throughout the monitoring period. Instead, the patient is free to place an electrode patch anywhere within the general region of the sternum, the area most likely to record high quality atrial signals or P-waves. In addition, power is provided through a battery provided on the electrode patch, which avoids having to either periodically open the housing of the monitor recorder for the battery replacement, which also creates the potential for moisture intrusion and human error, or to recharge the battery, which can potentially take the monitor recorder off line for hours at a time. In addition, the electrode patch is intended to be disposable, while the monitor recorder is a reusable component. Thus, each time that the electrode patch is replaced, a fresh battery is provided for the use of the monitor recorder. The wearable monitor further includes an air flow sensor and air flow telemetry can be collected contemporaneously with ECG data either with sensors contained on the underlying dermal patch or with a hub-and-spoke configuration that allows for either a direct sensor contact with the monitor or a wirelessly relayed transfer of air flow and pulmonary data to the central monitor.

One embodiment provides an extended wear electrocardiography and respiration-monitoring patch. The patch includes a flexible backing formed of an elongated strip of stretchable material with a narrow longitudinal midsection and, on each end, a contact surface at least partially coated with an adhesive dressing provided as a crimp relief; a pair of electrocardiographic electrodes conductively exposed on the contact surface of each end of the elongated strip, each of the electrocardiographic electrodes adapted to be positioned axially along the midline of the sternum for capturing action potential propagation; a non-conductive receptacle securely adhered on one end of the elongated strip opposite the contact surface and operable to removably receive an electrocardiography monitor, the non-conductive receptacle including electrode terminals aligned to electrically interface the pair of the circuit traces to the electrocardiography monitor; one or more respiratory sensors configured to interface with the electrocardiography monitor when the monitor is inserted into the non-conductive receptacle; and a flexible circuit affixed on each end of the elongated strip as a strain relief and including a pair of circuit traces electrically coupled to the pair of the electrocardiographic electrodes and a pair of the electrical pads, at least one of the circuit traces adapted to extend along the narrow longitudinal midsection to serve as the strain relief.

In a further embodiment, an extended wear electrocardiography patch with an extension for respiration monitoring is provided. The patch includes a flexible backing formed of an elongated strip of stretchable material with a narrow longitudinal midsection and, on each end, a contact surface at least partially coated with an adhesive dressing provided as a crimp relief; a pair of electrocardiographic electrodes conductively exposed on the contact surface of each end of the elongated strip, each of the electrocardiographic electrodes adapted to be positioned axially along the midline of the sternum for capturing action potential propagation; a non-conductive receptacle securely adhered on one end of the elongated strip opposite the contact surface and operable to removably receive an electrocardiography monitor, the non-conductive receptacle including electrode terminals aligned to electrically interface the pair of the circuit traces to the electrocardiography monitor; a tab extending from the flexible backing on which one or more respiratory sensors are positioned, the one or more respiratory sensors configured to interface with the electrocardiography monitor recorder when the recorder is inserted into the non-conductive receptacle; and a flexible circuit affixed on each end of the elongated strip as a strain relief and including a pair of circuit traces electrically coupled to the pair of the electrocardiographic electrodes and a pair of the electrical pads, at least one of the circuit traces adapted to extend along the narrow longitudinal midsection to serve as the strain relief.

In a still further embodiment, an extended wear electrocardiography patch with respiration-monitoring capabilities is provided. The patch includes a flexible backing formed of an elongated strip of stretchable material with a narrow longitudinal midsection and, on each end, a contact surface at least partially coated with an adhesive dressing provided as a crimp relief; a pair of electrocardiographic electrodes conductively exposed on the contact surface of each end of the elongated strip, each of the electrocardiographic electrodes adapted to be positioned axially along the midline of the sternum for capturing action potential propagation; a non-conductive receptacle securely adhered on one end of the elongated strip opposite the contact surface and operable to removably receive an electrocardiography monitor, the non-conductive receptacle including electrode terminals aligned to electrically interface the pair of the circuit traces to the electrocardiography monitor; one or more respiratory sensors located on a surface of the non-conductive receptacle, the one or more respiratory sensors configured to interface with the electrocardiography monitor when the monitor is inserted into the non-conductive receptacle; and a flexible circuit affixed on each end of the elongated strip as a strain relief and including a pair of circuit traces electrically coupled to the pair of the electrocardiographic electrodes and a pair of the electrical pads, at least one of the circuit traces adapted to extend along the narrow longitudinal midsection to serve as the strain relief.

The monitoring patch is especially suited to the female anatomy. The narrow longitudinal midsection can fit nicely within the intermammary cleft of the breasts without inducing discomfort, whereas conventional patch electrodes are wide and, if adhesed between the breasts, would cause chafing, irritation, frustration, and annoyance, leading to low patient compliance.

The foregoing aspects enhance ECG monitoring performance and quality facilitating long-term ECG recording, critical to accurate arrhythmia diagnosis.

In addition, the foregoing aspects enhance comfort in women (and certain men), but not irritation of the breasts, by placing the monitoring patch in the best location possible for optimizing the recording of cardiac signals from the atrium, another feature critical to proper arrhythmia diagnosis. And, such ECG recording systems can easily be interfaced with air flow and respiratory recording systems that can extend cephalad to the sternum for recording tracheal airflow and for monitoring respiratory rate and underlying dermal $SpO_2$ and $pCO_2$ measures, all features of pulmonary disorders.

Finally, the foregoing aspects as relevant to monitoring are equally applicable to recording other physiological measures, such as temperature, respiratory rate, blood sugar, oxygen saturation, and blood pressure, as well as other measures of body chemistry and physiology.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Long-term collection of air flow telemetry contemporaneous with collection of ECG data allows a physician interpreting physiological monitoring results to correlate abnormal respiratory and cardiac events, helping the physician in diagnosing the patient. Results of such a monitoring can be particularly useful for diagnosing sleep apnea conditions, which have both respiratory and cardiac components. For example, obstructive sleep apnea (OSA) is a disorder characterized by physical occlusion of upper airways during a patient's sleep, which causes either an apnea, a complete cessation of air flow, or a hypopnea, a partial cessation of air flow. An OSA episode causes the patient to transiently awaken to a lighter stage of sleep, the awakening followed by a restoration of the air flow. The occlusion causes a hypoxemia, an abnormal decrease in blood oxygen level, and is accompanied by strenuous respiratory efforts, such as thoracoabdominal movements, of the patient. OSA episodes may further be accompanied by cardiac arrhythmias. The hypoxemia is accompanied by a rise in peripheral sympathetic activity, which in turn may trigger a tachyarrhythmia once the patient's respiration resumes. The sympathetic activity may remain at a heightened level even during the patient's wakefulness, triggering further tachyarrhythmias. Furthermore, in some patients, the hypoxemia can be accompanied by cardiac parasympathetic activity, which can cause a profound nocturnal bradycardia.

Central sleep apnea (CSA), which can be a form of Cheyne-Stokes breathing, is similarly associated with cardiac abnormalities and has been estimated to occur in 30-40% of patients with heart failure. CSA is caused by a defect in central ventilatory control by the brain of the patient; due to the defect, the brain fails to send respiratory commands to the appropriate muscles, and the patient stops breathing. In contrast to OSA, the lack of respiratory commands results in respiratory efforts being absent during the OSA episode. As the patient stops breathing during a CSA episode, the patient develops hypoxemia and hypercapnia, an abnormal increase in blood carbon dioxide levels; due to the rising hypoxemia and hypercarpnia, the brain reinitiates breathing, with the breathing rate gradually rising until reaching the level of hyperpnea, abnormally deep breathing, which gradually ceases as the levels of blood oxygen and carbon dioxide are restored to normal. The patient's heart rate rises gradually with the rise of the respiration rate, and thus, the hyperpnea may trigger a tachyarrhythmia. Monitoring both air flow and cardiac activity of the patient allows to correlate the cardiac and respiratory abnormalities that OSA and CSA cause, and aid in diagnosing these conditions.

Figure 1:
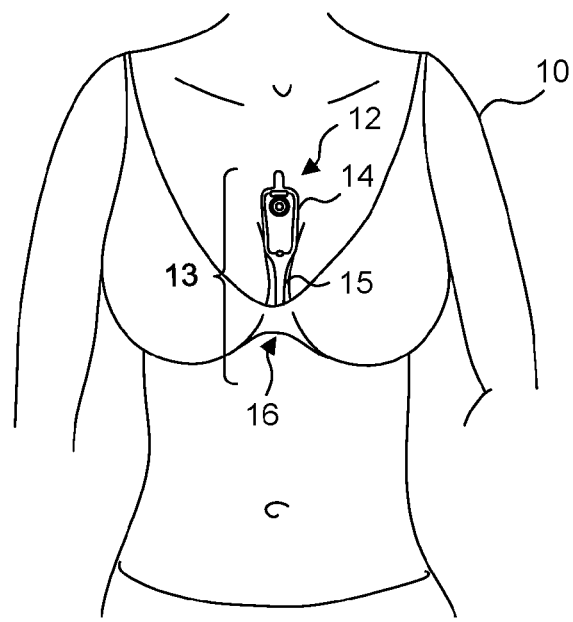
FIGS. 1 and 2 are diagrams showing, by way of examples, a self-contained personal air flow sensing monitor, including a monitor recorder in accordance with one embodiment, respectively fitted to the sternal region of a female patient and a male patient.
Figure 2:
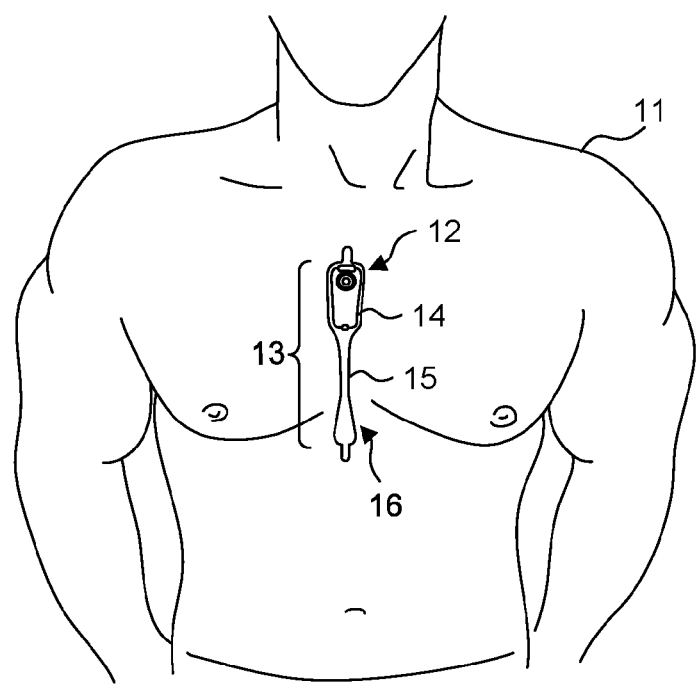

Physiological monitoring can be provided through a wearable monitor that includes two components, a flexible extended wear electrode patch and a removable reusable monitor recorder. FIGS. 1 and 2 are diagrams showing, by way of examples, a self-contained personal air flow sensing monitor 12, including a monitor recorder 14 in accordance with one embodiment, respectively fitted to the sternal region of a female patient 10 and a male patient 11. The wearable monitor 12 sits centrally (in the midline) on the patient's chest along the sternum 13 oriented top-to-bottom with the monitor recorder 14 preferably situated towards the patient's head. In a further embodiment, the orientation of the wearable monitor 12 can be corrected post-monitoring, as further described infra. The electrode patch 15 is shaped to fit comfortably and conformal to the contours of the patient's chest approximately centered on the sternal midline 16 (or immediately to either side of the sternum 13). The distal end of the electrode patch 15 extends towards the Xiphoid process and, depending upon the patient's build, may straddle the region over the Xiphoid process. The proximal end of the electrode patch 15, located under the monitor recorder 14, is below the manubrium and, depending upon patient's build, may straddle the region over the manubrium.

The placement of the wearable monitor 12 in a location at the sternal midline 16 (or immediately to either side of the sternum 13) significantly improves the ability of the wearable monitor 12 to cutaneously sense cardiac electric signals, particularly the P-wave (or atrial activity) and, to a lesser extent, the QRS interval signals in the ECG waveforms that indicate ventricular activity while simultaneously facilitating comfortable long-term wear for many weeks. The sternum 13 overlies the right atrium of the heart and the placement of the wearable monitor 12 in the region of the sternal midline 13 puts the ECG electrodes of the electrode patch 15 in a location better adapted to sensing and recording P-wave signals than other placement locations, say, the upper left pectoral region or lateral thoracic region or the limb leads. In addition, placing the lower or inferior pole (ECG electrode) of the electrode patch 15 over (or near) the Xiphoid process facilitates sensing of ventricular activity and provides superior recordation of the QRS interval.

Figure 3:
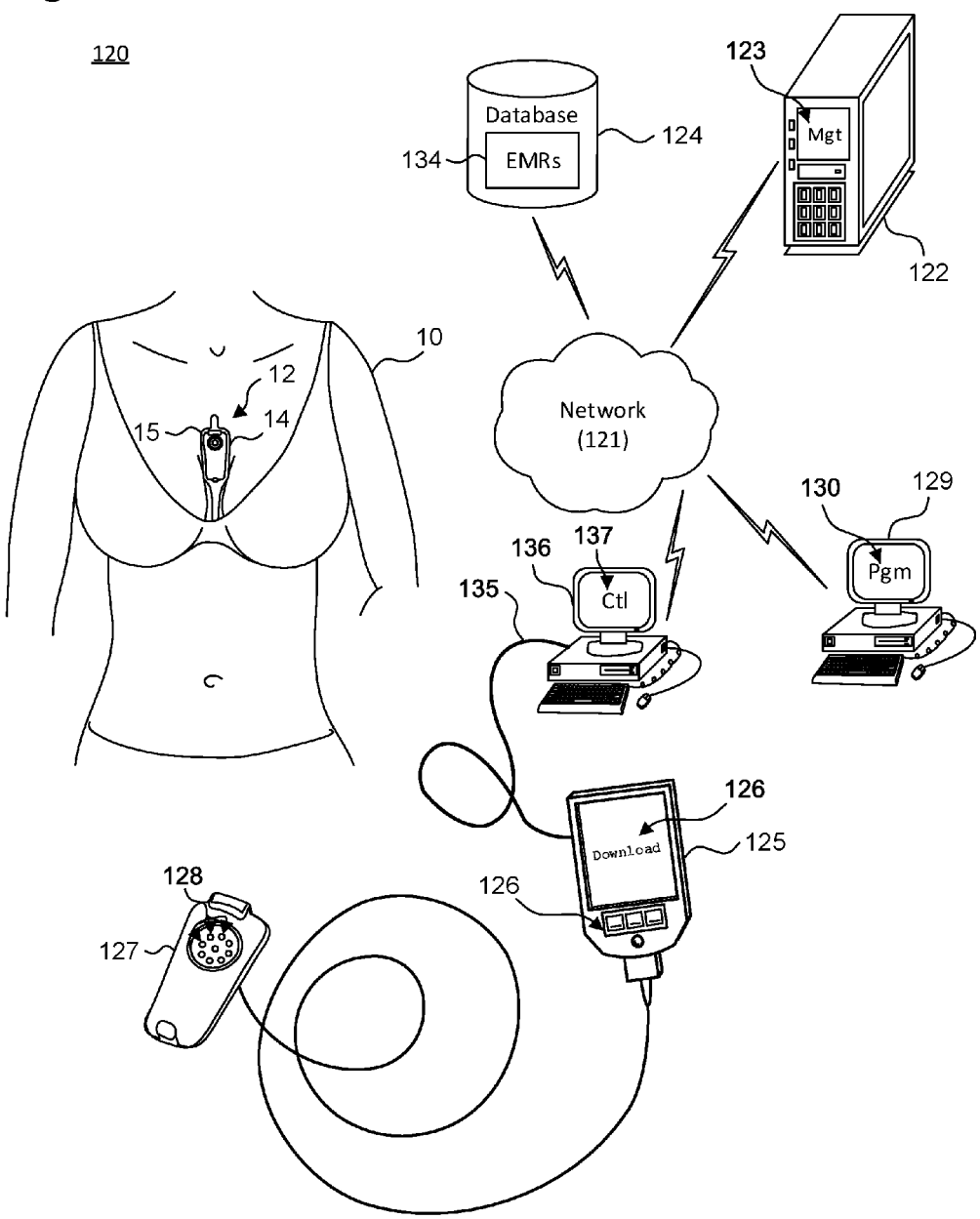
FIG. 3 is a perspective view showing a system for remote interfacing of a self-contained personal air flow sensing monitor in accordance with one embodiment inserted.

The monitor recorder 14 of the wearable air flow sensing monitor 12 senses and records the patient's air flow and ECG data into an onboard memory. In addition, the wearable monitor 12 can interoperate with other devices. FIG. 3 is a functional block diagram showing a system 120 for remote interfacing of a self-contained personal air flow sensing monitor 12 in accordance with one embodiment. The monitor recorder 14 is a reusable component that can be fitted during patient monitoring into a non-conductive receptacle provided on the electrode patch 15, as further described infra with reference to FIG. 4, and later removed for offloading of stored ECG data or to receive revised programming. Following completion of ECG and air flow monitoring, the monitor recorder 14 can the monitor recorder 14 can then be connected to a download station 125, which could be a programmer or other device that permits the retrieval of stored ECG monitoring data, execution of diagnostics on or programming of the monitor recorder 14, or performance of other functions. The monitor recorder 14 has a set of electrical contacts (not shown) that enable the monitor recorder 14 to physically interface to a set of terminals 128 on a paired receptacle 127 of the download station 125. In turn, the download station 125 executes a communications or offload program 126 ("Offload") or similar program that interacts with the monitor recorder 14 via the physical interface to retrieve the stored ECG monitoring data. The download station 125 could be a server, personal computer, tablet or handheld computer, smart mobile device, or purpose-built programmer designed specific to the task of interfacing with a monitor recorder 14. Still other forms of download station 125 are possible.

Figure 13:
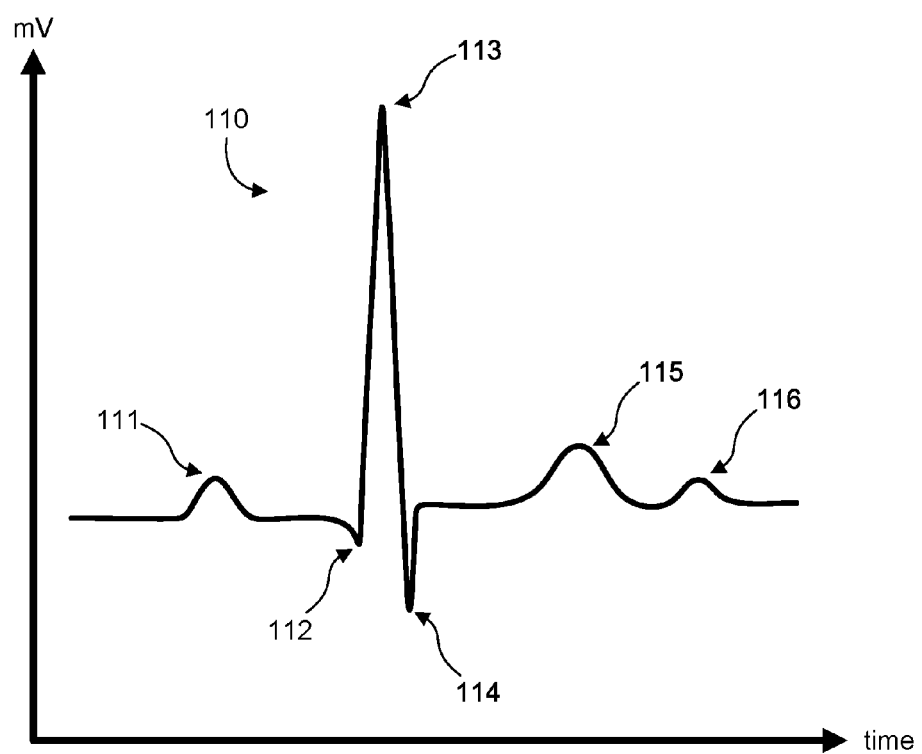
FIG. 13 is a graph showing, by way of example, a typical ECG waveform.
Figure 14:
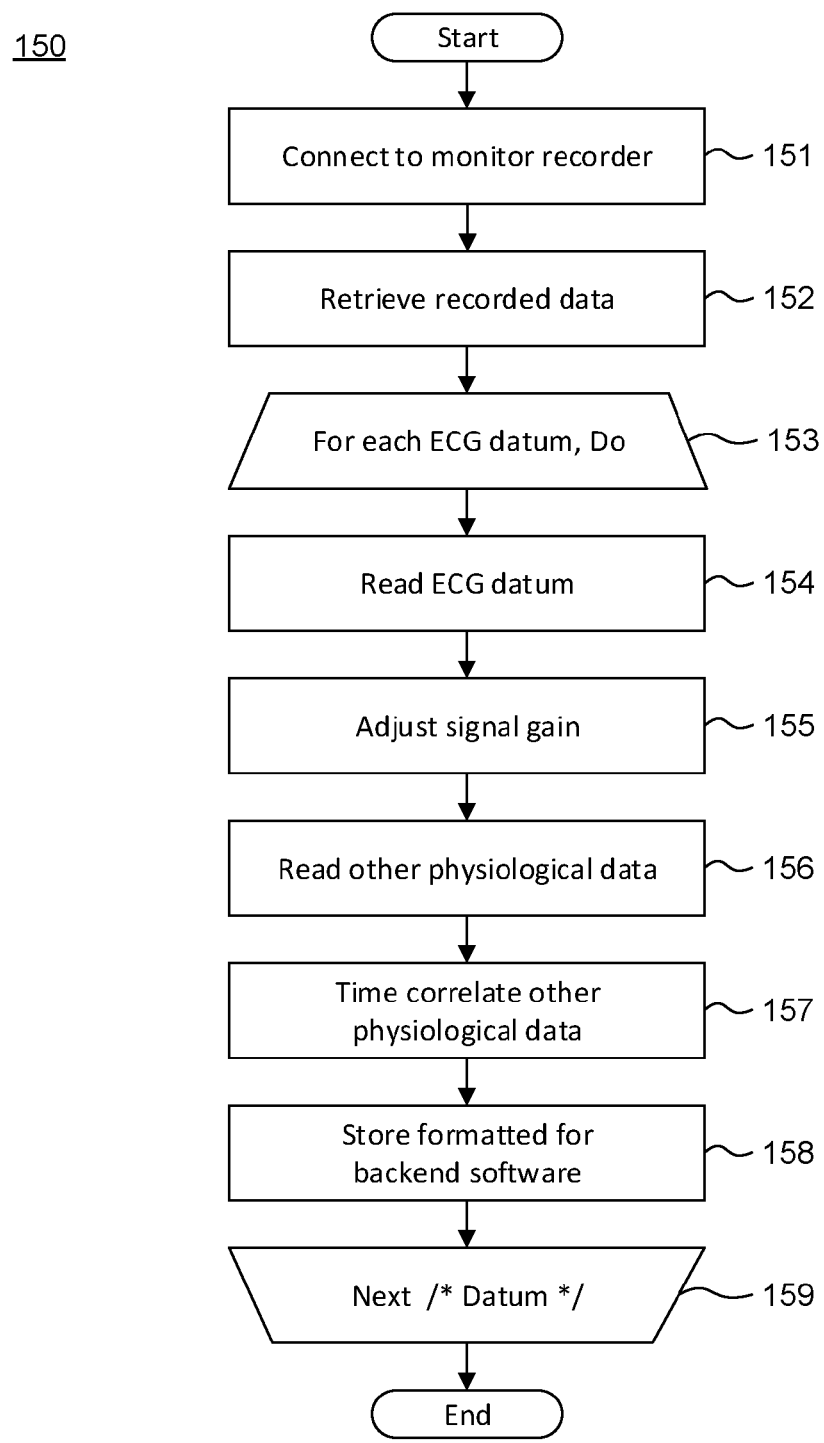
FIG. 14 is a flow diagram showing a method for offloading and converting ECG and other physiological data from a self-contained air flow sensing monitor in accordance with one embodiment.

Upon retrieving stored ECG monitoring data from a monitor recorder 14, middleware first operates on the retrieved data to adjust the ECG waveform, as necessary, and to convert the retrieved data into a format suitable for use by third party post-monitoring analysis software, as further described infra with reference to FIG. 14. The formatted data can then be retrieved from the download station 125 over a hard link 135 using a control program 137 ("Ctl") or analogous application executing on a personal computer 136 or other connectable computing device, via a communications link (not shown), whether wired or wireless, or by physical transfer of storage media (not shown). The personal computer 136 or other connectable device may also execute middleware that converts ECG data and other information into a format suitable for use by a third-party post-monitoring analysis program, as further described infra with reference to FIG. 13. Note that formatted data stored on the personal computer 136 would have to be maintained and safeguarded in the same manner as electronic medical records (EMRs) 134 in the secure database 124, as further discussed infra. In a further embodiment, the download station 125 is able to directly interface with other devices over a computer communications network 121, which could be some combination of a local area network and a wide area network, including the Internet, over a wired or wireless connection.

A client-server model could be used to employ a server 122 to remotely interface with the download station 125 over the network 121 and retrieve the formatted data or other information. The server 122 executes a patient management program 123 ("Mgt") or similar application that stores the retrieved formatted data and other information in a secure database 124 cataloged in that patient's EMRs 134. In addition, the patient management program 123 could manage a subscription service that authorizes a monitor recorder 14 to operate for a set period of time or under pre-defined operational parameters, such as described in commonly-assigned U.S. Patent Application Publication No.: 2015/0087950, pending, the disclosure of which is incorporated by reference.

The patient management program 123, or other trusted application, also maintains and safeguards the secure database 124 to limit access to patient EMRs 134 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 124. The physician would execute an application program 130 ("Pgm"), such as a post-monitoring ECG analysis program, on a personal computer 129 or other connectable computing device, and, through the application 130, coordinate access to his patient's EMRs 134 with the patient management program 123. Other schemes and safeguards to protect and maintain the integrity of patient EMRs 134 are possible.

Figure 4:
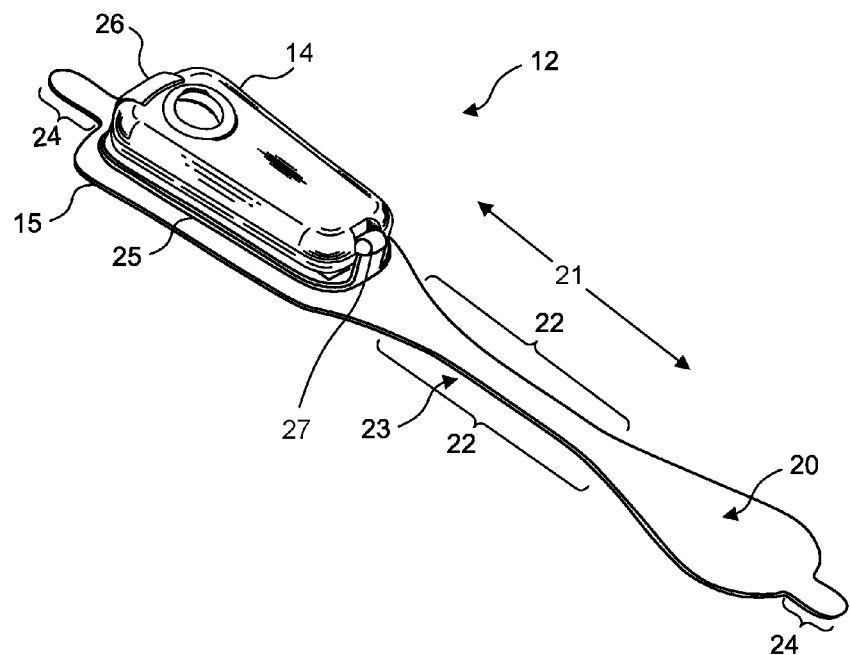
FIG. 4 is a perspective view showing an extended wear electrode patch with the monitor recorder in accordance with one embodiment.

During use, the electrode patch 15 is first adhesed to the skin along the sternal midline 16 (or immediately to either side of the sternum 13). A monitor recorder 14 is then snapped into place on the electrode patch 15 to initiate ECG monitoring. FIG. 4 is a perspective view showing an extended wear electrode patch 15 with a monitor recorder 14 inserted in accordance with one embodiment. The body of the electrode patch 15 is preferably constructed using a flexible backing 20 formed as an elongated strip 21 of wrap knit or similar stretchable material with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape, when viewed from above. The electrode patch 15 incorporates features that significantly improve wearability, performance, and patient comfort throughout an extended monitoring period. During wear, the electrode patch 15 is susceptible to pushing, pulling, and torqueing movements, including compressional and torsional forces when the patient bends forward, and tensile and torsional forces when the patient leans backwards. To counter these stress forces, the electrode patch 15 incorporates strain and crimp reliefs, such as described in commonly-assigned U.S. Patent Application Publication No.: 2015/0087948, pending, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the intermammary cleft between the breasts, especially in buxom women. The cut-outs 22 and longitudinal midsection 23 help the electrode patch 15 fit nicely between a pair of female breasts in the intermammary cleft. Still other shapes, cut-outs and conformities to the electrode patch 15 are possible. For example, an elongated tab may extend from the flexible backing, as further described infra with reference to FIGS. 17-19.

The monitor recorder 14 removably and reusably snaps into an electrically non-conductive receptacle 25 during use. The monitor recorder 14 contains electronic circuitry for recording and storing the patient's electrocardiography as sensed via a pair of ECG electrodes provided on the electrode patch 15, such as described in commonly-assigned U.S. Patent Application Publication No.: 2015/0087949, pending, the disclosure of which is incorporated by reference. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
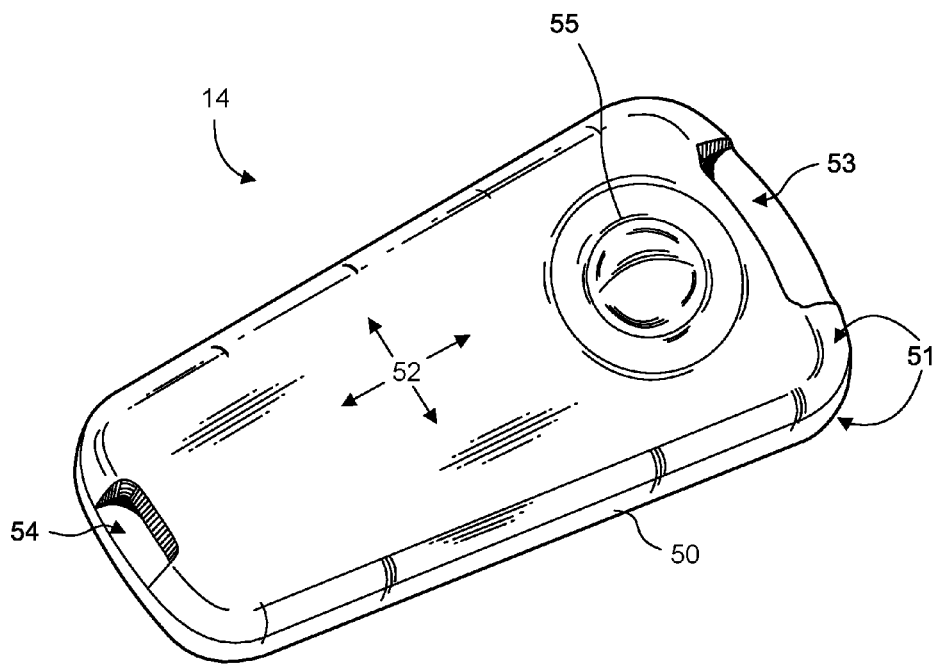
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52, when viewed from above, such as described in commonly-assigned U.S. Design Pat. No. D717,955, issued on Nov. 18, 2014, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to respectively engage the retention catch 26 and the tension clip 27 molded into non-conductive receptacle 25. Other shapes, features, and conformities of the sealed housing 50 are possible.

The electrode patch 15 is intended to be disposable. The monitor recorder 14, however, is reusable and can be transferred to successive electrode patches 15 to ensure continuity of monitoring. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin is able to recover from the wearing of an electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to reinitiate and continue the ECG monitoring.

Figure 6:
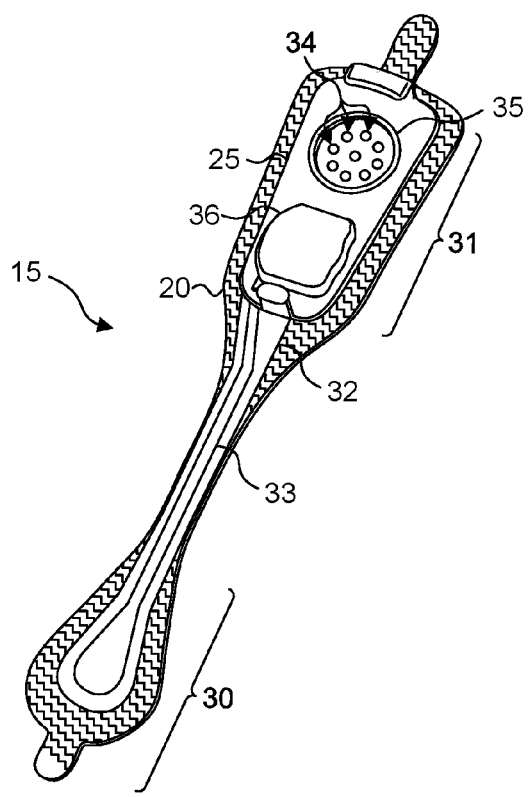
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 and a proximal circuit trace (not shown) electrically couple ECG electrodes (not shown) to a pair of electrical pads 34. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14, and the moisture-resistant seal 35 enables the monitor recorder 14 to be worn at all times, even during bathing or other activities that could expose the monitor recorder 14 to moisture.

In addition, a battery compartment 36 is formed on the bottom surface of the non-conductive receptacle 25, and a pair of battery leads (not shown) electrically interface the battery to another pair of the electrical pads 34. The battery contained within the battery compartment 35 can be replaceable, rechargeable or disposable.

Figure 7:
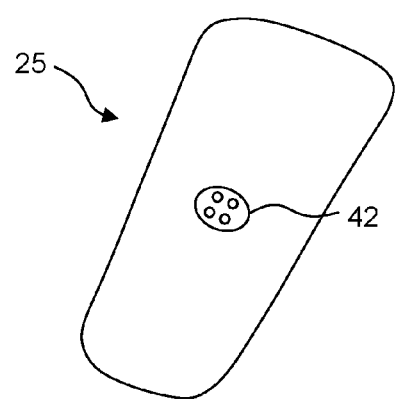
FIG. 7 is an alternative view of the non-conductive receptacle 25 of FIG. 6.

The air flow monitor 12 can monitor a patient's physiology, including both the patient's air flow and ECG. FIG. 7 is an alternative perspective view of the non-conductive receptacle 25 in accordance with one embodiment, showing an air flow sensor 42 included on the surface of non-conductive receptacle 25 that faces the flexible backing 20. The air flow sensor 42 includes a microphone that is positioned to detect sounds of breathing of the patient through the patient's sternum 13. The microphone may also be able to record sounds associated with the breathing, such as snoring. The microphone can be a MicroElectrical-Mechanical System (MEMS) microphone, though other types of microphones can be used in a further embodiment. In a further embodiment, the air flow sensor can be located in a different part of the electrode patch 15. In a still further embodiment, the air flow sensor 42 can be located on the monitor recorder 14. While the air flow sensor is shown to be the only component present on the surface of the non-conductive receptacle, other components may also be present on the surface. For example, an SPO2 sensor to measure blood oxygen level (not shown) can be included on the surface. In one embodiment, the SPO2 sensor can include a reflectance pulse oximetry sensor; in a further embodiment, a transmissive pulse oximetry may be included as part of the SPO2 sensor. Similarly, a $pCO_2$ sensor (not shown) to measure blood carbon dioxide level may also be included on the surface. In addition, a respiratory rate sensor can be located on the surface of the non-conductive receptacle 25. In one embodiment, the respiratory rate sensor can include a strain gauge, with parts of the strain gauge extending beyond the material of the non-conductive receptacle 25 and the flexible backing 20, and contacting the patient's skin. The respiratory rate sensor can detect patient respiration and may further be able to detect an amplitude of the chest movements during the respiration, which may assist in determining whether respiratory efforts are present during an apneic episode. In one embodiment, the parts of the gauge contacting the skin, the "arms," may be adhered to the skin, making the gauge capable of detecting expansion and contraction of the patient's chest as well as pauses between the chest movements. In a further embodiment, the respiratory rate sensor can include a transthoracic impedance sensor. All of the sensors on the surface can also be located in other parts of the patch 15.

Figure 17:
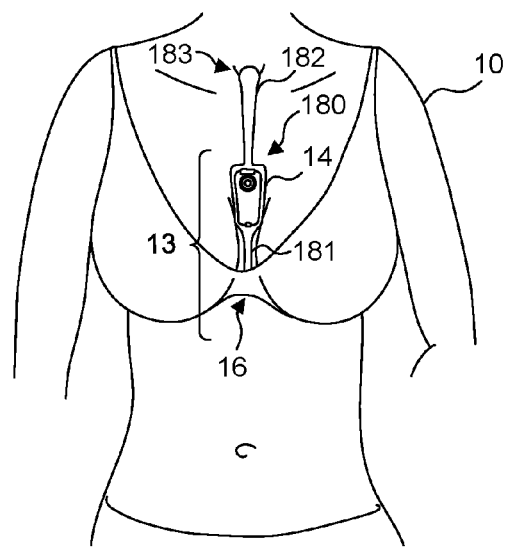
FIG. 17 is a diagram showing, by way of example, a self-contained personal air flow sensing monitor fitted to the sternal region of a female patient in accordance with a further embodiment.

While the self-contained air flow sensing monitor as shown in FIG. 4 is capable of long-term collection of air flow and ECG data, the monitor can be further modified for an improved air flow monitoring. For example, the extended wear patch may be further modified to provide improved access to sounds of breathing in the patient's trachea. FIG. 17 is a diagram showing, by way of example, a self-contained personal air flow sensing monitor 180 fitted to the sternal region of a female patient 10 in accordance with a further embodiment, with a modified, elongated extended wear electrode patch 181. The patch 181 includes an elongated tab 182, the tab 182 extending over the patient's sternal notch 183. The extended tab 182 reaching over the sternal notch 183 allows improved air flow telemetry detection, with an air flow sensor being placed over the sternal notch 13. This placement allows the air flow sensor to detect sounds from the trachea of the patient 10, which may provide improved quality of the air flow telemetry. The monitor recorder 14 stores the recorded air flow telemetry as described supra and infra.

Figure 18:
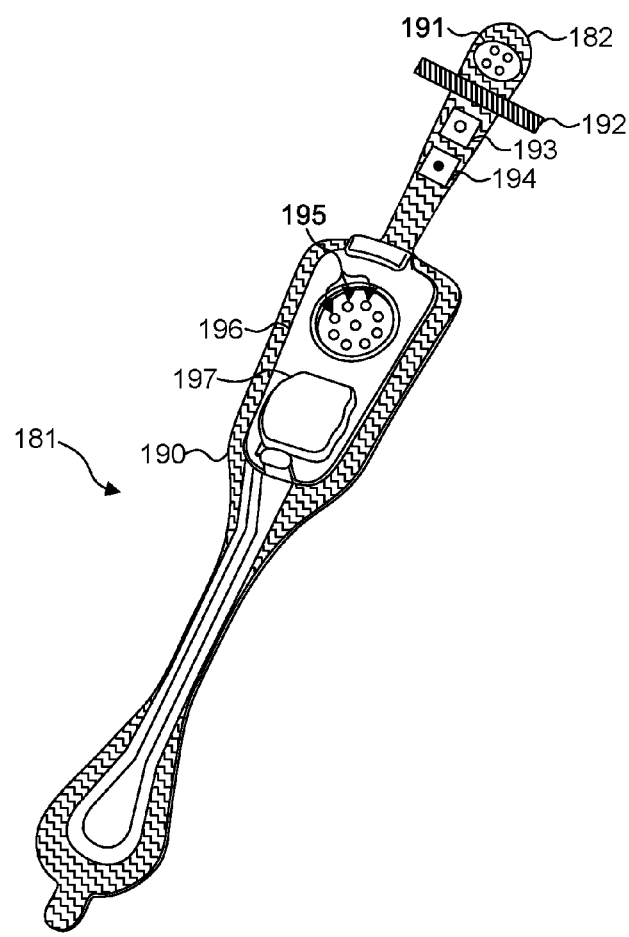
FIG. 18 is a perspective view showing the extended wear electrode patch with an elongated tab in accordance with one embodiment without the monitor inserted in accordance with one embodiment.

FIG. 18 is a perspective view showing the extended wear electrode patch with an elongated tab in accordance with one embodiment without the monitor 14 inserted. The length and other dimensions of the extended tab 182 may vary depending on the height of the patient and the tab 182 is of sufficient length to reach the patient's sternal notch 183. The tab 182 can be made of the same material as the flexible backing 190, and be a continuous piece of stretchable material with the backing 190. While shown as having as widening towards a rounded proximal end, other shapes of the tab 182 are also possible. Still other shapes and configurations of the tab 182 are possible.

An air flow sensor 191, which includes the microphone as described above, can be located near the proximal end of the tab 182, allowing the sensor 191 to detect tracheal breathing sounds through the sternal notch 183. In a further embodiment, the air flow sensor can be located in another part of the tab 182. Other sensors can also be located on extended tab 182, such as a respiratory rate sensor 192, SPO2 sensor 193, and pCO$_2$ sensor 194. In the embodiment where the respiratory sensor includes a strain gauge, the strain gauge may extend beyond the materials of the tab 182, contacting the patient's skin, and allowing the gauge to measure movements of the patient's chest. In a further embodiment, the other sensors may be collected at other parts of the patch 181, as further described with reference to FIG. 19. The recorded telemetry from the sensors can be transmitted to the electrical pads 195 of the non-conductive receptacle 196 over wiring included in the patch 180, allowing the monitor recorder 14 to receive the telemetry through the electric pads 195 once the monitor recorder is snapped into the non-conductive receptacle 196. The sensors 191-195 can be electrically connected to the battery 197, or be powered from another source. In a further embodiment, the sensors located on the extended tab 182 can be electrically connected to a wireless transceiver (not shown), and can transmit the recorded telemetry over the wireless transceiver to the monitor recorder 14. In the described embodiment, the extended tab 182 can be at least partially covered with adhesive to facilitate the attachment of the patch to the sternal node. Similarly, the parts of the respiratory rate sensor contacting the patient's skin may further be covered with an adhesive. While the extended tab 182 can affect the placement of sensors and the shape of the patch 181, unless otherwise mentioned, configurations and characteristics of the embodiment of the monitor 180 can be the same as described above and below in regards to the embodiment of the self-contained air flow sensing monitor shown with reference to FIG. 4, and the data collected by the embodiment of the monitor 180 can be processed in the same way as the data collected by the embodiment of the monitor shown in FIG. 4.

Figure 19:
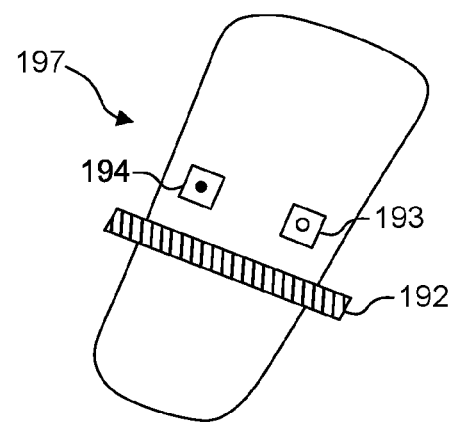
FIG. 19 shows an alternative perspective view of the non-conductive receptacle of FIG. 18 in accordance with one embodiment

As mentioned above, in the electrode patch shown in FIG. 18, respiratory sensors other than the air flow sensor 191 can be included either on the elongated tab 182 or on other parts of the patch 181. FIG. 19 shows an alternative perspective view of the non-conductive receptacle 196 of FIG. 18 in accordance with one embodiment, showing the surface of the non-conductive receptacle 196 that faces the flexible backing 190. The respiratory rate sensor 192, SPO2 sensor 193, and pCO$_2$ sensor 194 can be located on the surface of the non-conductive receptacle, though other locations for these sensors are also possible. In the embodiment where the respiratory rate sensor 192 is a strain gauge, the arms of the gauge may extend beyond the receptacle 196, contacting the patient's skin and allowing to the movement of the patient's chest.

Figure 8:
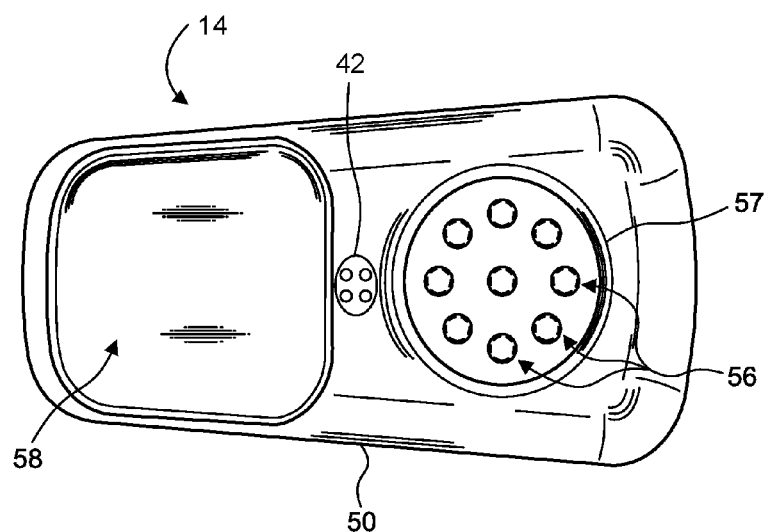
FIG. 8 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 8 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25. In the further embodiment where the air flow sensor 42 is located on the monitor recorder 14, the air flow sensor 42 can also be located on the bottom surface, though other locations are possible.

The placement of the flexible backing 20 on the sternal midline 16 (or immediately to either side of the sternum 13) also helps to minimize the side-to-side movement of the wearable monitor 12 in the left- and right-handed directions during wear. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that respectively facilitates compression and twisting of the flexible backing 20 in response to compressional and torsional forces. Other forms of flexible backing crimp reliefs are possible.

Figure 9:
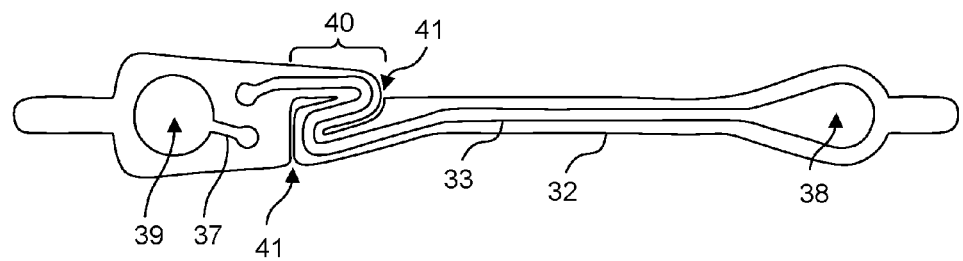
FIG. 9 is a top view showing the flexible circuit of the extended wear electrode patch of FIG. 4 when mounted above the flexible backing.

Unlike the flexible backing 20, the flexible circuit 32 is only able to bend and cannot stretch in a planar direction. The flexible circuit 32 can be provided either above or below the flexible backing 20. FIG. 9 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to tensile and torsional forces. A pair of strain relief cutouts 41 partially extend transversely from each opposite side of the flexible circuit 32 and continue longitudinally towards each other to define in 'S'-shaped pattern, when viewed from above. The strain relief respectively facilitates longitudinal extension and twisting of the flexible circuit 32 in response to tensile and torsional forces. Other forms of circuit board strain relief are possible.

Figure 10:
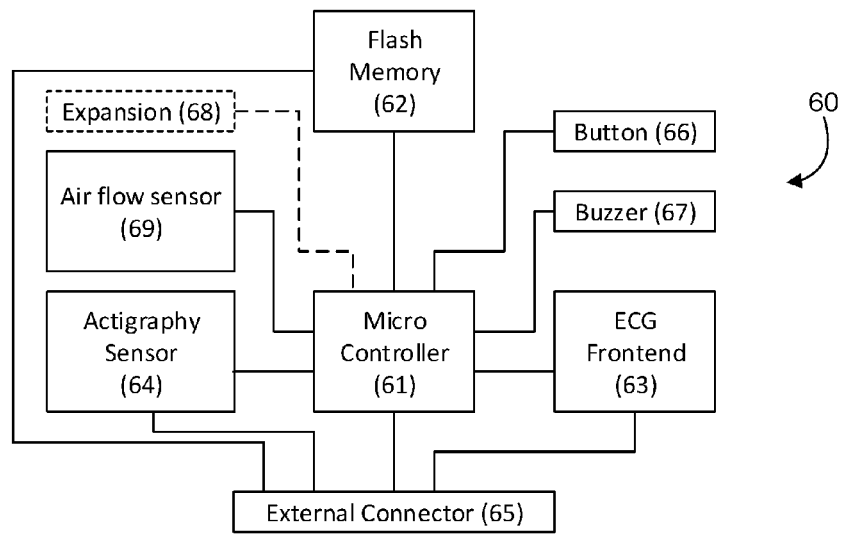
FIG. 10 is a functional block diagram showing the component architecture of the circuitry of the monitor recorder of FIG. 4.

ECG monitoring and other functions performed by the monitor recorder 14 are provided through a micro controlled architecture. FIG. 10 is a functional block diagram showing the component architecture of the circuitry 60 of the monitor recorder 14 of FIG. 4. The circuitry 60 is externally powered through a battery provided in the non-conductive receptacle 25 (shown in FIG. 6). Both power and raw ECG signals, which originate in the pair of ECG electrodes 38, 39 (shown in FIG. 9) on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and which physically and electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or download station (not shown), follow the same electrical pin assignment convention to facilitate interoperability. The external connector 65 also serves as a physical interface to a download station 125 that permits the retrieval of stored ECG monitoring data, communication with the monitor recorder 14, and performance of other functions.

Operation of the circuitry 60 of the monitor recorder 14 is managed by a microcontroller 61. The micro-controller 61 includes a program memory unit containing internal flash memory that is readable and writeable. The internal flash memory can also be programmed externally. The microcontroller 61 draws power externally from the battery provided on the electrode patch 15 via a pair of the electrical contacts 56. The microcontroller 61 connects to the ECG front end circuit 63 that measures raw cutaneous electrical signals and generates an analog ECG signal representative of the electrical activity of the patient's heart over time.

The circuitry 60 of the monitor recorder 14 also includes a flash memory 62, which the micro-controller 61 uses for storing ECG monitoring data and other physiology and information. The flash memory 62 also draws power externally from the battery provided on the electrode patch 15 via a pair of the electrical contacts 56. Data is stored in a serial flash memory circuit, which supports read, erase and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

The circuitry 60 of the monitor recorder 14 further includes an actigraphy sensor 64 implemented as a 3-axis accelerometer. The accelerometer may be configured to generate interrupt signals to the microcontroller 61 by independent initial wake up and free fall events, as well as by device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event occurrence analyses, such as described in commonly-assigned U.S. Patent Application Publication No.: 2015/0087923, pending, the disclosure of which is incorporated by reference.

The microcontroller 61 includes an expansion port that also utilizes the communications bus. External devices, such as the air flow sensor 69, separately drawing power externally from the battery provided on the electrode patch 15 or other source, can interface to the microcontroller 61 over the expansion port in half duplex mode. For instance, an external physiology sensor can be provided as part of the circuitry 60 of the monitor recorder 14, or can be provided on the electrode patch 15 with communication with the microcontroller 61 provided over one of the electrical contacts 56. The physiology sensor can include an $SpO_2$ sensor, a $pCO_2$ sensor, blood pressure sensor, temperature sensor, glucose sensor, respiratory rate sensor, air flow sensor, volumetric pressure sensing, or other types of sensor or telemetric input sources. For instance, in the embodiment where the air flow sensor 69 is included as part of the monitor recorder 14, the air flow sensor 69 is incorporated into the circuitry 60 and interfaces the micro-controller 61 over the expansion port in half duplex, and may be configured to generate interrupt signals to the microcontroller 61 when detecting an air flow event, as further discussed infra with reference to FIG. 12. Similarly, other respiratory sensors such as the $SpO_2$ sensor, a $pCO_2$ sensor, and a respiratory rate sensor, can be connected to the micro-controller 61 in the same way and generate an interrupt signal upon detecting a respiratory event. In a further embodiment, a wireless interface for interfacing with other wearable (or implantable) physiology monitors, as well as data offload and programming, can be provided as part of the circuitry 60 of the monitor recorder 14, or can be provided on the electrode patch 15 with communication with the micro-controller 61 provided over one of the electrical contacts 56, such as described in commonly-assigned U.S. Patent Application Publication No.: 2015/0087921, pending, the disclosure of which is incorporated by reference.

Finally, the circuitry 60 of the monitor recorder 14 includes patient-interfaceable components, including a tactile feedback button 66, which a patient can press to mark events or to perform other functions, and a buzzer 67, such as a speaker, magnetic resonator or piezoelectric buzzer. The buzzer 67 can be used by the microcontroller 61 to output feedback to a patient such as to confirm power up and initiation of ECG monitoring. Still other components as part of the circuitry 60 of the monitor recorder 14 are possible.

Figure 11:
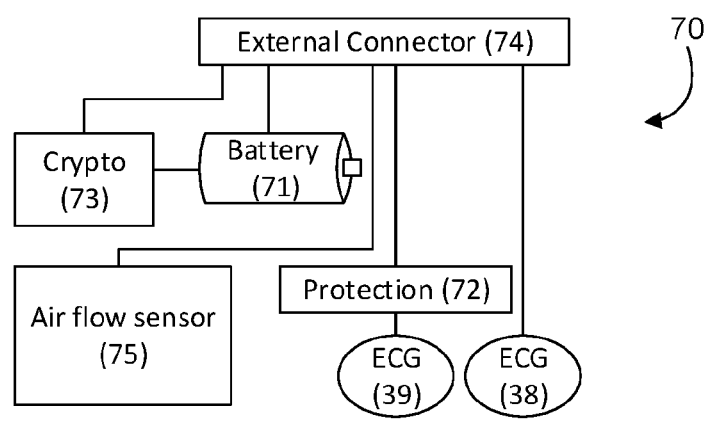
FIG. 11 is a functional block diagram showing the circuitry of the extended wear electrode patch of FIG. 4.

While the monitor recorder 14 operates under micro control, most of the electrical components of the electrode patch 15 operate passively. FIG. 11 is a functional block diagram showing the circuitry 70 of the extended wear electrode patch 15 of FIG. 4. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, the locating of the battery 71 physically on the electrode patch 15 lowers the center of gravity of the overall wearable monitor 12 and thereby helps to minimize shear forces and the effects of movements of the patient and clothing. Moreover, the housing 50 of the monitor recorder 14 is sealed against moisture and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance, quality, and duration of use. Finally, the architecture of the monitor recorder 14 is open, in that other physiology sensors or components can be added by virtue of the expansion port of the microcontroller 61. Requiring those additional sensors or components to draw power from a source external to the monitor recorder 14 keeps power considerations independent of the monitor recorder 14. Thus, a battery of higher capacity could be introduced when needed to support the additional sensors or components without effecting the monitor recorders circuitry 60.

In the embodiment where the air flow sensor 75 is a part of the electrode patch 15, the air flow sensor 75 is included as a part of the circuitry 70 and can draw power from the battery 71. In this embodiment, the air flow sensor 75 is connected to the external connector 74, and may be configured to generate interrupt signals to the microcontroller 61 when detecting an air flow event, as further discussed infra with reference to FIG. 12. Other respiratory sensors, such as the $SpO_2$ sensor, the $pCO_2$ sensor, and the respiratory rate sensor can be included as part of the circuitry 70 in the same manner as the air flow sensor 69.

Second, the pair of ECG electrodes 38, 39 respectively provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14, such as described in commonly-assigned U.S. Patent Application Publication No.: 2015/0087950, pending, the disclosure which is incorporated by reference.

Figure 12:
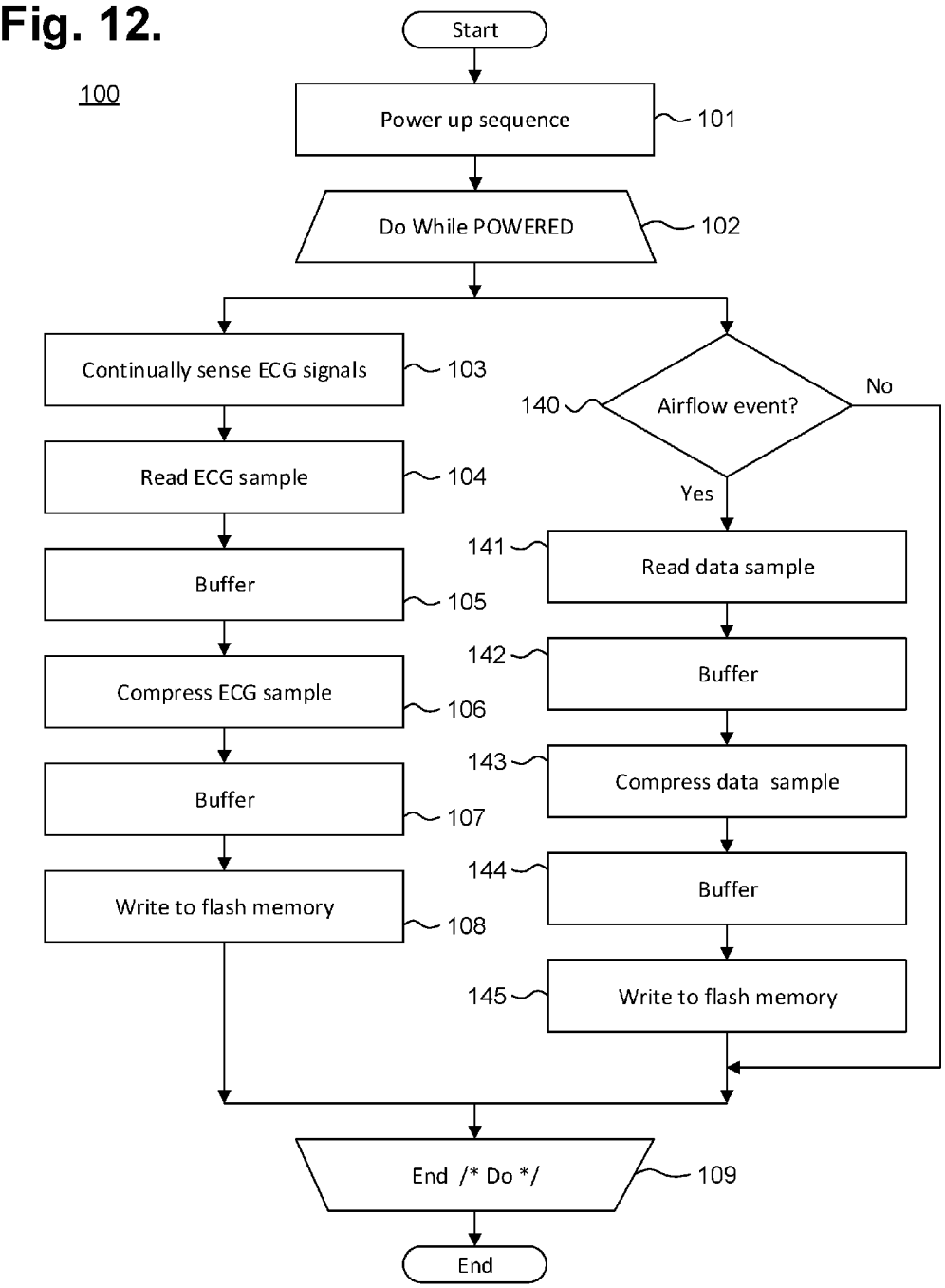
FIG. 12 is a flow diagram showing a monitor recorder-implemented method for monitoring ECG and air flow data for use in the monitor recorder of FIG. 4.

The monitor recorder 14 continuously monitors the patient's heart rate and physiology. FIG. 12 is a flow diagram showing a monitor recorder-implemented method 100 for monitoring ECG and air flow data for use in the monitor recorder 14 of FIG. 4. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Following satisfactory completion of the power up sequence, an iterative processing loop (steps 102-109) is continually executed by the microcontroller 61. During each iteration (step 102) of the processing loop, the ECG frontend 63 (shown in FIG. 10) continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal output front end 63. FIG. 12 is a graph showing, by way of example, a typical ECG waveform 110. The x-axis represents time in approximate units of tenths of a second. The y-axis represents cutaneous electrical signal strength in approximate units of millivolts. The P-wave 111 has a smooth, normally upward, that is, positive, waveform that indicates atrial depolarization. The QRS complex usually begins with the downward deflection of a Q wave 112, followed by a larger upward deflection of an R-wave 113, and terminated with a downward waveform of the S wave 114, collectively representative of ventricular depolarization. The T wave 115 is normally a modest upward waveform, representative of ventricular depolarization, while the U wave 116, often not directly observable, indicates the recovery period of the Purkinje conduction fibers.

Sampling of the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time and abnormalities in the PR interval can reveal underlying heart disorders, thus representing another reason why the P-wave quality achievable by the self-contained personal air flow sensing monitor described herein is medically unique and important. The long-term observation of these ECG indicia, as provided through extended wear of the wearable monitor 12, provides valuable insights to the patient's cardiac function and overall well-being.

Each sampled ECG signal, in quantized and digitized form, is temporarily staged in buffer (step 105), pending compression preparatory to storage in the flash memory 62 (step 106). Following compression, the compressed ECG digitized sample is again buffered (step 107), then written to the flash memory 62 (step 108) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

The monitor recorder 14 also receives data from the air flow sensor 42. The data is received in a conceptually-separate execution thread as part of the iterative processing loop (steps 102-109) continually executed by the microcontroller 61. Patient's air flow is monitored by the air flow sensor 42, and the air flow sensor 42 determines presence of an air flow event, an air flow abnormality potentially indicative of a medical condition, that needs to be recorded as part of the monitoring (step 140). The abnormalities in air flow to be recorded include both interruptions of airflow, such as apneas and hypopneas, as well increased air flow due to, for example, deepening of the patient's breathing during a hyperpnea. The presence of the interruption of air flow can be detected by either a complete lack of a sound of breathing, or, for a partial interruption, by a weakening below a certain threshold of a strength of the sound signal detected. Similarly, when the frequency of breathing sounds becomes greater than a predefined threshold, an increased air flow can be detected. Other techniques to detect air flow abnormalities can be used. If the duration of an air flow abnormality exceeds a temporal threshold, the abnormality is determined to be an air flow event (step 140). The temporal threshold can be 10 seconds, which is the length at which an air flow interruption is classified as an apnea or a hypopnea, though other temporal thresholds can be used. If no abnormalities are detected or they do not rise to a level of an air flow event (step 140), the method 100 proceeds to step 109. A detection of an air flow event (140) causes the air flow signal to generate an interrupt signal to the microcontroller 61, triggering further processing of the event as described below. During each iteration (step 102) of the processing loop, if air flow event data is detected (step 140), a sample of the air flow telemetry is read (step 141) by the microcontroller 61 and, if necessary, converted into a digital signal by the onboard ADC of the microcontroller 61. Each air flow event data sample, in quantized and digitized form, is temporarily staged in buffer (step 142), pending compression preparatory to storage in the flash memory subsystem 62 (step 143). Following compression, the compressed air flow data sample is again buffered (step 144), then written to the flash memory 62 (step 145) using the communications bus. Processing continues (step 109), so long as the monitoring recorder 14 remains connected to the electrode patch 15 (and storage space remains available in the flash memory 62), after which the processing loop is exited and execution terminates. Still other operations and steps are possible.

While the method 100 is described with reference to detecting an air flow event, abnormal physiological events detected by other respiratory sensors, such as the respiratory rate sensor 192, SpO$_2$ sensor 193, and pCO$_2$ sensor 194 can be recorded using similar steps. For example, a respiratory rate sensor would detect a respiratory rate event upon the rate of respiration, or the amplitude of movement of the patient's chest during the patient's respiration, rising above or falling below a certain threshold for a certain duration of time. An oxygen level event can be determined upon the patient's blood oxygen level as measured by the SpO$_2$ 193 sensor rising above or falling below a certain threshold. Similarly, a carbon dioxide level event can be determined upon the carbon dioxide level as measured by the pCO$_2$ 194 sensor rising above or falling below a certain threshold. Upon the event detection, the event would be processed as described with regards to air flow 141-145 mutatis mutandis. Respiratory events collected by these additional respiratory sensors, the respiratory rate sensor 192, the SpO$_2$ sensor 193, and the pCO$_2$ sensor 194, further aid a physician interpreting monitoring results in diagnosing an abnormal condition.

The monitor recorder 14 stores ECG data and other information in the flash memory subsystem 62 (shown in FIG. 10) using a proprietary format that includes data compression. As a result, data retrieved from a monitor recorder 14 must first be converted into a format suitable for use by third party post-monitoring analysis software. FIG. 14 is a flow diagram showing a method 150 for remote interfacing of a self-contained personal air flow sensing monitor 12 in accordance with one embodiment. The method 150 can be implemented in software and execution of the software can be performed on a download station 125, which could be a programmer or other device, or a computer system, including a server 122 or personal computer 129, such as further described supra with reference to FIG. 3, as a series of process or method modules or steps. For convenience, the method 150 will be described in the context of being performed by a personal computer 136 or other connectable computing device (shown in FIG. 3) as middleware that converts ECG data and other information into a format suitable for use by a third-party post-monitoring analysis program. Execution of the method 150 by a computer system would be analogous mutatis mutandis.

Initially, the download station 125 is connected to the monitor recorder 14 (step 151), such as by physically interfacing to a set of terminals 128 on a paired receptacle 127 or by wireless connection, if available. The data stored on by the monitor recorder 14, including ECG and physiological monitoring data, other recorded data, and other information are retrieved (step 152) over a hard link 135 using a control program 137 ("Ctl") or analogous application executing on a personal computer 136 or other connectable computing device. The data retrieved from the monitor recorder 14 is in a proprietary storage format and each datum of recorded ECG monitoring data, as well as any other physiological data or other information, must be converted, so that the data can be used by a third-party post-monitoring analysis program. Each datum of ECG monitoring data is converted by the middleware (steps 153-159) in an iterative processing loop. During each iteration (step 153), the ECG datum is read (step 154) and, if necessary, the gain of the ECG signal is adjusted (step 155) to compensate, for instance, for relocation or replacement of the electrode patch 15 during the monitoring period. In addition, depending upon the configuration of the wearable monitor 12, other physiological data (or other information), including patient events, such as air flow events, fall, peak activity level, sleep detection, detection of patient activity levels and states and so on, may be recorded along with the ECG monitoring data is read (step 156) and is time-correlated to the ECG monitoring data (step 157). For instance, air flow events recorded by the air flow events recorded by the air flow sensor 42 would be temporally matched to the ECG data to provide the proper physiological context to the sensed event occurrence. Similarly, actigraphy data may have been sampled by the actigraphy sensor 64 based on a sensed event occurrence, such as a sudden change in orientation due to the patient taking a fall. In response, the monitor recorder 14 will embed the actigraphy data samples into the stream of data, including ECG monitoring data, that is recorded to the flash memory 62 by the micro-controller 61. Post-monitoring, the actigraphy data is temporally matched to the ECG data to provide the proper physiological context to the sensed event occurrence. As a result, the three-axis actigraphy signal is turned into an actionable event occurrence that is provided, through conversion by the middleware, to third party post-monitoring analysis programs, along with the ECG recordings contemporaneous to the event occurrence. Other types of processing of the other physiological data (or other information) are possible.

Thus, during execution of the middleware, any other physiological data (or other information) that has been embedded into the recorded ECG monitoring data is read (step 156) and time-correlated to the time frame of the ECG signals that occurred at the time that the other physiological data (or other information) was noted (step 157). Finally, the ECG datum, signal gain adjusted, if appropriate, and other physiological data as time correlated are stored in a format suitable to the backend software (step 158) used in post-monitoring analysis.

In a further embodiment, the other physiological data, if apropos, is embedded within an unused ECG track. For example, the SCP-ENG standard allows multiple ECG channels to be recorded into a single ECG record. The monitor recorder 14, though, only senses one ECG channel. The other physiological data can be stored into an additional ECG channel, which would otherwise be zero-padded or altogether omitted. The backend software would then be able to read the other physiological data in context with the single channel of ECG monitoring data recorded by the monitor recorder 14, provided the backend software implemented changes necessary to interpret the other physiological data. Still other forms of embedding of the other physiological data with formatted ECG monitoring data, or of providing the other physiological data in a separate manner, are possible.

Processing continues (step 159) for each remaining ECG datum, after which the processing loop is exited and execution terminates. Still other operations and steps are possible.

Figure 15:
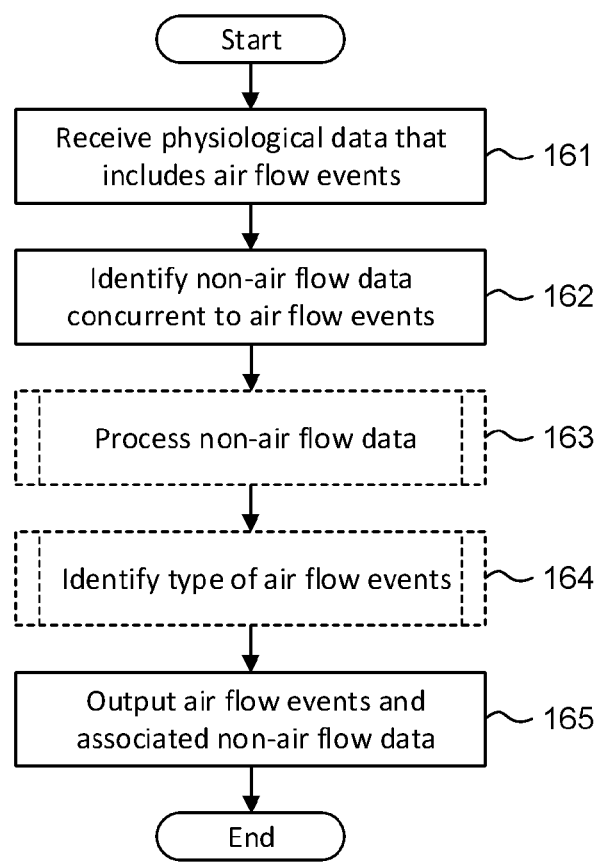
FIG. 15 is a flow diagram showing method for processing data collected by the self-contained personal air flow sensing monitor in accordance with one embodiment.

The collection of the ECG data as described above, and as described in a commonly assigned U.S. Patent Application Publication No.: 2015/0087949, pending, the disclosure of which is incorporated by reference, allows acquisition of ECG data collected over an extended period of time, and when combined the recording of air flow events, simplifies monitoring for episodes of cardiorespiratory conditions. The data collected by the monitor 12 and downloaded to the download station 125 can be further processed by the application software 130 to correlate the air flow events with ECG and other non-air flow data physiological data, which can be helpful to a physician in diagnosing the patient. FIG. 15 is a flow diagram showing the method 160 for processing data collected by the self-contained personal air flow sensing monitor 12 in accordance with one embodiment. Physiological data that includes the identified air flow events, and non-air flow data, including the ECG data and, if applicable, data collected by other sensors of the monitor 12, is received by the application software 130 (step 161). The non-air flow physiological data collected approximately concurrently to the airflow events is identified (step 162). The approximately concurrent data can include not only data that was collected at the same time as when the air flow events took place, but also data collected within a specified time interval from a beginning or an end of each of the air flow events. Optionally, the identified concurrent data can be processed to detect other physiological events, such as cardiac arrhythmias, approximately contemporaneous to air flow events (step 163). For example, the sampled ECG signals can be processed to identify a presence of a cardiac arrhythmia that is substantially contemporaneous to the air flow events. For example, a heart rate in excess of 100 beats per minute (bpm) can indicate a tachyarrhythmia, and temporal intervals where the heart rate exceeds the 100 bpm threshold can be marked as an event indicative of a tachyarrhythmia. Similarly, a heart rate falling below 60 bpm can be indicative of a bradyarrhythmia, and temporal intervals where the patient's heart rate exceeds 60 bpm can be marked as events indicative of a bradyarrhythmia. Similarly, the substantially contemporaneous actigraphy data can also be processed to detect actigraphy events, as further described in detail in commonly-assigned U.S. Patent Application Publication No.: 2015/0087923, pending, the disclosure of which is incorporated by reference. Other ways to process the non-air flow data are possible. The occurrence of arrhythmias concurrent with respiratory problems can indicate the diagnosis of serious sleep apnea. While the method 160 is described with reference to processing data from a monitoring that has already concluded, in a further embodiment, the processing can be performed on the air flow monitor 12, and the occurrence of arrhythmias concurrent with respiratory problems can also serve as a source of initiating an alarm system for patient awareness and alerting the patient with an auditory alert or vibratory alert on the monitor itself, such as through the use of the buzzer 67.

Figure 16:
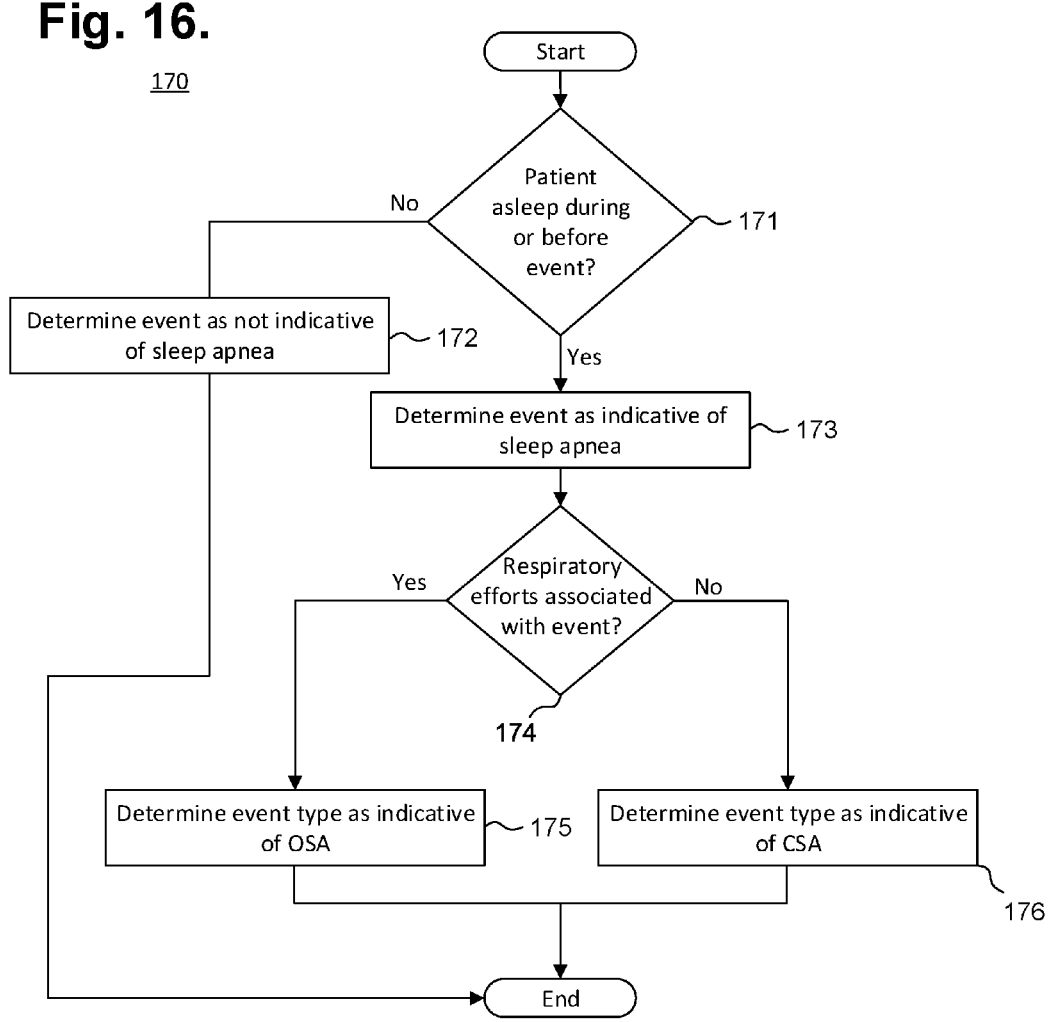
FIG. 16 is a flow diagram showing a routine for identifying a type of an air flow event for use in the method of FIG. 15 in accordance with one embodiment.

Following the optional identification of the contemporaneous data, the type of the air flow event can be detected (step 164), as further described with reference to FIG. 16. Finally, the information about the air flow events and approximately concurrent non-air flow data is output to a user, such as a physician, such as though a screen of a personal computer 129 (step 165). The output information can include the time the events occurred, the duration of the events, the nature of the event (interruption of air flow or an increased air flow), the magnitude of the air flow abnormality during the event, the type of the event, as well as information about the identified concurrent non-air flow physiological data. In a further embodiment, the sounds recorded during the events, such as snoring can also be output. Any events identified based on the non-air flow data can also be output to the user. In a further embodiment, non-air flow physiological data that is not substantially contemporaneous to the air flow events is also output to the user.

Identification of a type of an air flow event can provide further help to the physician interpreting the results in diagnosing the patient. FIG. 16 is a flow diagram showing a routine 170 for identifying a type of an air flow event for use in the method 160 of FIG. 15. As sleep apnea air flow events occur during a patient's sleep or upon awakening, when respiration resumes, whether the patient was asleep during or immediately prior to an air flow event is important to diagnosing sleep apnea. Whether the patient was asleep approximately concurrently to an air flow event, which includes the period of time during the event or in a predefined temporal interval before the event, is determined by the application software 130 (step 171). The determination can be made using the data collected by the actigraphy sensor 64, which monitors the patient's posture and movement rate. When the actigraphy sensor 64 data shows that the patient assumed a recumbent position and the patient's movement rate has fallen below a predefined threshold, the application software 130 can determine that the patient has fallen asleep. Other physiological data can also be used to determine if the patient is asleep. For example, falling asleep is characterized by a gradual decrease of the patient's heart rate. By obtaining an average of the heart rate of the patient when the patient is awake, either by analyzing the ECG data and other physiological data collected during the monitoring or from another source, the application software 130 can mark a gradual decline in heart rate from that level as the patient falling asleep. Other ways to determine whether the patient is asleep are possible. If the event occurs when the patient is not asleep and has not been within the predefined temporal period before the event (step 171), the event is determined as not indicative of a sleep apnea condition (step 172), and the routine 170 ends. If the patient is asleep during the event (step 171), the application software 130 determines the event to be indicative of a sleep apnea condition (step 173). The application further determines whether respiratory efforts are associated with the event (step 174). For apneic or hypopneic events, the association is present when the event is accompanied by respiratory efforts. For hyperpneic events, the association is present when the hyperpneic event was preceded within a predefined time interval by an apneic or hypopneic event accompanied by respiratory efforts. The presence of respiratory efforts can be determined using the data collected the respiratory rate sensor 192 or the actigraphy sensor 64, with the presence of chest movements during an air flow event being indicative of respiratory efforts. In a further embodiment, the respiratory efforts can be detected based on data collected by an impedance pneumograph included as one of the physiological sensors of the monitor 12, which can detect chest movements. Other ways to determine the presence of the respiratory efforts are possible.

If the respiratory efforts are associated with the event (step 174), the application determines the event type to be indicative of an OSA condition (step 175), terminating the routine 170. If the respiratory efforts are not associated with the event (step 176), the application determines the event to be indicative of a CSA condition (step 175), terminating the routine 150. While the routine 170 is described in relation to a sleep apnea condition, in a further embodiment, the application software can be used to identify other types of respiratory events.

While the invention has been particularly shown and described as referenced to the embodiments thereof, those skilled in the art will understand that the foregoing and other changes in form and detail may be made therein without departing from the spirit and scope.

What is claimed is:
1. An extended wear electrocardiography and respiration-monitoring patch, comprising:
   a flexible backing formed of an elongated strip of stretchable material with a narrow longitudinal midsection and, on each end, a contact surface at least partially coated with an adhesive dressing provided as a crimp relief;

a pair of electrocardiographic electrodes conductively exposed on the contact surface of each end of the elongated strip, each of the electrocardiographic electrodes adapted to be positioned axially along the midline of the sternum for capturing action potential propagation;

a non-conductive receptacle securely adhered on one end of the elongated strip opposite the contact surface and operable to removably receive an electrocardiography monitor, the non-conductive receptacle comprising electrode terminals aligned to electrically interface the pair of the circuit traces to the electrocardiography monitor;

one or more respiratory sensors configured to interface with the electrocardiography monitor when the monitor is inserted into the non-conductive receptacle; and a flexible circuit affixed on each end of the elongated strip as a strain relief and comprising a pair of circuit traces electrically coupled to the pair of the electrocardiographic electrodes and a pair of the electrical pads, at least one of the circuit traces adapted to extend along the narrow longitudinal midsection to serve as the strain relief.

2. An extended wear electrocardiography and respiration monitoring patch according to claim 1, further comprising:
a tab extending from the flexible backing on which one or more of the respiratory sensors are comprised.

3. An extended wear electrocardiography and respiration monitoring patch according to claim 1, wherein the one or more of the respiratory sensors are located on a surface of the non-conductive receptacle that faces the flexible backing.

4. A self-contained personal air flow sensing monitor according to claim 1, wherein the one or more respiratory sensors further comprise at least one of an air flow sensor, an $SpO_2$ sensor, a $pCO_2$ sensor, and a respiratory rate sensor.

5. An extended wear electrocardiography and respiration monitoring patch according to claim 1, further comprising:
a battery compartment provided in the non-conductive receptacle and comprising a pair of battery leads electrically coupleable to a battery; and
the non-conductive receptacle further comprising power terminals aligned to electrically interface the pair of battery leads to the electrocardiography monitor.

6. An extended wear electrocardiography patch with an extension for respiration monitoring, comprising:
a flexible backing formed of an elongated strip of stretchable material with a narrow longitudinal midsection and, on each end, a contact surface at least partially coated with an adhesive dressing provided as a crimp relief;
a pair of electrocardiographic electrodes conductively exposed on the contact surface of each end of the elongated strip, each of the electrocardiographic electrodes adapted to be positioned axially along the midline of the sternum for capturing action potential propagation;
a non-conductive receptacle securely adhered on one end of the elongated strip opposite the contact surface and operable to removably receive an electrocardiography monitor, the non-conductive receptacle comprising electrode terminals aligned to electrically interface the pair of the circuit traces to the electrocardiography monitor;
a tab extending from the flexible backing on which one or more respiratory sensors are comprised, the one or more respiratory sensors configured to interface with the electrocardiography monitor recorder when the recorder is inserted into the non-conductive receptacle; and
a flexible circuit affixed on each end of the elongated strip as a strain relief and comprising a pair of circuit traces electrically coupled to the pair of the electrocardiographic electrodes and a pair of the electrical pads, at least one of the circuit traces adapted to extend along the narrow longitudinal midsection to serve as the strain relief.

7. An extended wear electrocardiography patch according to claim 6, wherein the respiratory sensor comprises an air flow sensor.

8. An extended wear electrocardiography patch according to claim 7, wherein the air flow sensor comprises a microphone.

9. An extended wear electrocardiography patch according to claim 7, wherein the extended tab is of a sufficient length to reach a sternal notch of the patient when the electrodes are positioned along the midline of the sternum and the air flow sensor is located on a portion of the tab located over the sternal notch when the electrodes are positioned along the midline of the sternum.

10. An extended wear electrocardiography patch according to claim 6, wherein the one or more respiratory sensors comprise a respiratory rate sensor.

11. An extended wear electrocardiography patch according to claim 6, wherein the respiratory rate sensor comprises a strain gauge comprising two arms extending beyond the tab and shaped to contact the patient's skin when the electrodes are positioned along the midline of the sternum.

12. An extended wear electrocardiography patch according to claim 6, wherein the one or more respiratory sensors further comprise one or more of an $SpO_2$ sensor and a $pCO_2$ sensor.

13. An extended wear electrocardiography patch according to claim 6, wherein the tab comprises a continuous piece of stretchable material.

14. An extended wear electrocardiography patch according to claim 6, wherein the one or more respiratory are configured to wirelessly interface with the electrocardiography monitor when the monitor is inserted into the non-conductive receptacle.

15. An extended wear electrocardiography patch according to claim 6, wherein at least a portion of the tab is covered with an adhesive.

16. An extended wear electrocardiography patch with respiration-monitoring capabilities, comprising:
a flexible backing formed of an elongated strip of stretchable material with a narrow longitudinal midsection and, on each end, a contact surface at least partially coated with an adhesive dressing provided as a crimp relief;
a pair of electrocardiographic electrodes conductively exposed on the contact surface of each end of the elongated strip, each of the electrocardiographic electrodes adapted to be positioned axially along the midline of the sternum for capturing action potential propagation;
a non-conductive receptacle securely adhered on one end of the elongated strip opposite the contact surface and operable to removably receive an electrocardiography monitor, the non-conductive receptacle comprising electrode terminals aligned to electrically interface the pair of the circuit traces to the electrocardiography monitor;

one or more respiratory sensors located on a surface of the non-conductive receptacle, the one or more respiratory sensors configured to interface with the electrocardiography monitor when the monitor is inserted into the non-conductive receptacle; and a flexible circuit affixed on each end of the elongated strip as a strain relief and comprising a pair of circuit traces electrically coupled to the pair of the electrocardiographic electrodes and a pair of the electrical pads, at least one of the circuit traces adapted to extend along the narrow longitudinal midsection to serve as the strain relief.

17. An extended wear electrocardiography patch according to claim 16, wherein the surface of the non-conductive receptacle faces the flexible backing.

18. An extended wear electrocardiography patch according to claim 16, wherein the one or more respiratory sensors located on the surface comprise a microphone.

19. An extended wear electrocardiography patch according to claim 16, wherein the one or more respiratory sensors further comprise at least one of an $SpO_2$ sensor, a $pCO_2$ sensor, and a respiratory rate sensor.

20. An extended wear electrocardiography patch according to claim 16, wherein the respiratory rate sensor comprises a strain gauge comprising two arms extending beyond the flexible backing and shaped to contact the patient's skin when the electrodes are positioned along the midline of the sternum.

* * * * *